United States Patent
Howarth

(10) Patent No.: US 10,247,727 B2
(45) Date of Patent: Apr. 2, 2019

(54) PEPTIDE TAG SYSTEM THAT SPONTANEOUSLY FORM AN IRREVERSIBLE LINK TO PROTEIN PARTNERS VIA ISOPEPTIDE BONDS

(71) Applicant: Oxford University Innovation Limited, Oxford (GB)

(72) Inventor: Mark Howarth, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 139 days.

(21) Appl. No.: 15/359,796

(22) Filed: Nov. 23, 2016

(65) Prior Publication Data

US 2017/0146522 A1 May 25, 2017

Related U.S. Application Data

(62) Division of application No. 13/578,070, filed as application No. PCT/GB2011/000188 on Feb. 11, 2011, now Pat. No. 9,547,003.

(30) Foreign Application Priority Data

Feb. 11, 2010 (GB) .................................... 1002362

(51) Int. Cl.
  *G01N 33/531* (2006.01)
  *C07K 14/315* (2006.01)
  *C07K 7/08* (2006.01)
  *G01N 33/53* (2006.01)

(52) U.S. Cl.
  CPC ............. *G01N 33/531* (2013.01); *C07K 7/08* (2013.01); *C07K 14/315* (2013.01); *G01N 33/5306* (2013.01); *C07K 2319/21* (2013.01); *C07K 2319/70* (2013.01)

(58) Field of Classification Search
  None
  See application file for complete search history.

(56) References Cited

U.S. PATENT DOCUMENTS

| 5,773,577 A | 6/1998 | Cappello |
| 2009/0117113 A1 | 5/2009 | Bensi et al. |
| 2010/0150943 A1 | 6/2010 | Grandi et al. |
| 2013/0053544 A1 | 2/2013 | Howarth |

OTHER PUBLICATIONS

Bedbrook et al.; "Genetically Encoded Spy Peptide Fusion System to Detect Plasma Membrane-Localized Proteins in Vivo"; Chemistry & Biology; 22; pp. 1108-1121; (2015).
Budzik et al.; "Intramolecular Amide Bonds Stabilize Pili on the Surface of Bacilli"; PNAS USA; 106(47); pp. 19992-19997; (2007).
Definition of "disulphide bond"; in Lackie, John M., Dictionary of Cell and Molecular Biology, Kidlington, GBR, Academic Press; p. 127 (2015).
Definition of "eupeptide bond" in Lackie, John M. Dictionary of Cell and Molecular Biology, Kidlington, GBR: Academic Press, p. 151; (2007).
Definition of "isopeptide bond" in Lackie, John M., Dictionary of Cell and Molecular Biology, Kidlington, GBR: Academic Press, p. 225; (2007).
Definition of "isopeptide bond"; from Oxford Dictionary of Biochemistry and Molecular Biology; 2nd Ed, R. Cammack ed.; Oxford University Press; 2006.
Dong et al.; "Characterization of T Cell Epitopes Restricted by HLA-DP9 in Streptococcal M12 Protein"; Journal of Immunology; 154(9) pp. 4536-4545; (1995).
El Mortaji et al., "Stability and Assembly of Pilus Subunits of *Streptococcus pneumoniae*"; J. Biol. Chem.; 285(16); pp. 12405-12415; (2010).
Forsgren et al.; "Two Intramolecular Isopeptide Bonds are Identified in the Crystal Structure of the *Streptococcus gordonii* SspB C-terminal Domain"; J. Mol. Biol.; 397(3); pp. 740-751; (2010).
Hagan et al., "NMR and Theoretical Analysis of a Spontaneously Formed Lys-Asp Isopeptide Bond**". Agnew Chem Int Ed Engl.; pp. 8421-8425; (2010).
Hu, et al., "Autocatalytic Intramolecular Isopeptide Bond Formation in Gram-Positive Bacterial Pili: A QM/MM Simulation"; Journal of the American Chemical Society; 133(3); pp. 478-485; (2011).
International Search Report and Written Opinion; International Application No. PCT/GB2011/000188; International Filing Date Feb. 11, 2011; dated Apr. 20, 2011; 16 pages.
Izore et al.; "Structural Basis of Host Cell Recognition by the Pilus Adhesin from *Streptococcus pneumoniae*"; Structure; 18(1); pp. 106-115; (2010).
Kang et al.; "Intramolecular Isopeptide Bonds Give Thermodynamic and Proteolytic Stability to the Major Pilin Protein of *Streptococcus pyogenes*"; Journal of Biological Chemistry; 284(31); pp. 20729-20737; (2009).
Kang et al.; "Intramolecular Isopeptide Bonds: Protein Crosslinks Build for Stress?"; Trends in Biochemical Sciences; 36(4); pp. 229-237; (2011).

(Continued)

*Primary Examiner* — Suzanne M Noakes
(74) *Attorney, Agent, or Firm* — Cantor Colburn LLP

(57) ABSTRACT

Described herein is-a protein capable of spontaneously forming an isopeptide bond for the development of a peptide tag and binding partner pair wherein the peptide tag and binding partner are capable of covalently binding to each other via an isopeptide bond. Also provided is a method for developing a peptide tag and binding partner pair which are capable of covalently binding to each other based on a protein which is capable of spontaneously forming an isopeptide bond. Additionally provided are peptide tag and binding partner pairs which are obtainable from isopeptide proteins. Further, specifically developed peptide tags and binding partners are described, together with nucleic acid molecules and vectors which encode those peptides or proteins.

4 Claims, 13 Drawing Sheets

Specification includes a Sequence Listing.

(56) References Cited

OTHER PUBLICATIONS

Kang et al.; "The Corynebacterium Diphtheriae Shaft Pilin SpaA is Bilt of Tandem Ig-like Modules with Stabilizing Isopeptide and Disulfide Bonds"; PNAS US; 106(40); pp. 16967-16971; (2009).

Kang, et al.; "Stabilizing Isopeptide Bonds Revealed in Gram-Positive Bacterial Pilus Structure"; Science; 318; pp. 1625-1628 (2007).

Mayadas et al.; "In vitro Multimerization of Von Willebrand Factor is Triggered by Low pH: Importance of the Propolypeptide and free Sulfhydryls"; The Journal of Biological Chemistry 264(23); pp. 13497-13505; (1989).

Nylander et al.; "Structure of the C-terinal Domain of the Surface Antigen SpaP From the Caries Pathogen *Streptococcus* Mutans"; Acta Crystallogr Sect F Struct Biol Cryst Commum.; 67(Pt1); pp. 23-26; (2011).

Oke, et al.; "The Scottish Structural Proteomics Facility: Targets, Methods and Outputs"; J. Struct Funct Genomics; 11 (2); pp. 167-180; (2010).

Pointon et al.; "A Highly Unusual Thioester Bond in a Pilus Adhesin Is Required for Efficient Host Cell Interaction*"; J. Biol. Chem.; 285(44); pp. 33858-33866; (2010).

Sletten et al.; "Bioorthogonal Chemistry: Fishing for Selectivity in a Sea of Functionality"; Angew. Chem. Int. Ed.; 48; pp. 6974-6998; (2009).

Tominaga, et al.; "Design of a Specific Peptide Tag That Affords Covalent and Site-Specific Enzyme Immobilization Catalyzed by Microbial Transglutaminase"; Biomacromolecules; 6(4); pp. 2299-2304; (2005).

Wikoff et al.; "Topologically Linked Protein Rings in the Bacteriophage HK97 Capsid"; Science; 289; pp. 2129-2133; (2000).

Zakeri et al.; "Peptide Tag Forming a Rapid Covalent Bond to a Protein Through Engineering a Bacterial Adhesin"; PNAS; 109(12); pp. E690-E697; (2012).

Zakeri et al.; "Spontaneous Intermolecular Amide Bond Formation Between Side Chains for Irreversible Peptide Targeting"; Journal of the American Chemical Society; 132(13); pp. 4526-4527; (2010).

SEQ ID NO. 1 (NCBI Entrez Accession Code: AAK33238):

MKLRHLLLTGAALTSFAATTVHGETVVNGAKLTVTKNLDLVNSNALIPNTDFTFKIEPDTTVNEDGNKFKGVALNTPMTK
VTYTNSDKGGSNTKTAEFDFSEVTFEKPGVYYYKVTEEKIDKVPGVSYDTTSYTVQVHVLWNEEQQKPVATYIVGYKEGS
KVPIQFKNSLDSTTLTVKKKVSGTGGDRSKDFNFGLTLKANQYYKASEKVMIEKTTKGGQAPVQTEASIDQLYHFTLKDG
ESIKVTNLPVGVDYVVTEDDYKSEKYTTNVEVSPQDGAVKNIAGNSTEQETSTDKDMTITFTNKKDFEVPTGVAMTVAPY
IALGIVAVGGALYFVKKKNA

SEQ ID NO. 2 (NCBI Entrez Accession Code: AE004092 Region: 119650..120672):

ATGAAATTACGTCACTTACTATTAACGGGAGCAGCCCTAACTAGTTTTGCTGCTACAACAGTTCACGGGGAGACTGTTGT
AAACGGAGCCAAACTAACAGTTACAAAAAACCTTGATTTAGTTAATAGCAATGCATTAATTCCAAATACAGATTTTACAT
TTAAAATCGAACCTGATACTACTGTCAACGAAGACGGAAATAAGTTTAAAGGTGTAGCTTTGAACACACCGATGACTAAA
GTCACTTACACCAATTCAGATAAAGGTGGATCAAATACGAAAACTGCAGAATTTGATTTTTCAGAAGTTACTTTTGAAAA
ACCAGGTGTTTATTATTACAAAGTAACTGAGGAGAAGATAGATAAAGTTCCTGGTGTTTCTTATGATACAACATCTTACA
CTGTTCAAGTTCATGTCTTGTGGAATGAAGAGCAACAAAAACCAGTAGCTACTTATATTGTTGGTTATAAAGAAGGTAGT
AAGGTGCCAATTCAGTTCAAAAATAGCTTAGATTCTACTACATTAACGGTGAAGAAAAAGTTTCAGGTACCGGTGGAGA
TCGCTCTAAAGATTTTAATTTTGGTCTGACTTTAAAAGCAAATCAGTATTATAAGGCGTCAGAAAAAGTCATGATTGAGA
AGACAACTAAAGGTGGTCAAGCTCCTGTTCAAACAGAGGCTAGTATAGATCAACTCTATCATTTTACCTTGAAAGATGGT
GAATCAATCAAAGTCACAAATCTTCCAGTAGGTGTGGATTATGTTGTCACTGAAGACGATTACAAATCAGAAAAATATAC
AACCAACGTGGAAGTTAGTCCTCAAGATGGAGCTGTAAAAAATATCGCAGGTAATTCAACTGAACAAGAGACATCTACTG
ATAAAGATATGACCATTACTTTTACAAATAAAAAAGACTTTGAAGTGCCAACAGGAGTAGCAATGACTGTGGCACCATAT
ATTGCTTTAGGAATTGTAGCAGTTGGTGGAGCTCTTTACTTTGTTAAAAAGAAAAATGCTTAA

SEQ ID NO. 3 (NCBI Entrez Accession Code: NP_814829):

MTKSVKFLVLLLVMILPIAGALLIGPISFGAELSKSSIVDKVELDHTTLYQGEMTSIKVSFSDKENQKIK
PGDTITLTLPDALVGMTENDSSPRKINLNGLGEVFIYKDHVVATFNEKVESLHNVNGHFSFGIKTLITNS
SQPNVIETDFGTATATQRLTIEGVTNTETGQIERDYPFFYKVGDLAGESNQVRWFLNVNLNKSDVTEDIS
IADRQGSGQQLNKESFTFDIVNDKETKYISLAEFEQQGYGKIDFVTDNDFNLRFYRDKARFTSFIVRYTS
TITEAGQHQATFENSYDINYQLNNQDATNEKNTSQVKNVFVEGEASGNQNVEMPTEEESLDIPLETIDEWE
PKTPTSEQATETSEKTDTTETAESSSQPEVHVSPTEEENPDEGETLGTIEPIIPEKPSVTTEENGTTETAE
SSQPEVHVSPTEEENPDESETLGTIEPIIPEKPSVTTEENGTTETAESSQPEVHVSPAEEENPDESETLG
TILPILPEKFSVTTEENGTTETAESSQPEVHVSPTEEENPDESETLGTIAPIIPEKPSVTTEENGTTETA
ESSQPEVHVSPTKEITTTEKKQPSTETTVEKNKNVTSKNQPQILNAPLNTLKNEGSPQLAPQLLSEPIQK
LNEANGQRELPKTGTTKTPFMLIAGILASTFAVLGVSYLQIPKN

SEQ ID NO. 4 (NCBI Entrez Accession Code: NC_004668 Region:
1068036..1070060):

ATGACAAAAAGTGTAAAATTTTTAGTGTTACTGTTGGTAATGATTCTACCAATTGCGGGGGCGTTATTGA
TTGGTCCAATTTCGTTTGGCGCCGAATTGAGCAAAAGTTCAATCGTTGACAAAGTAGAATTAGATCACAC
TACTTTATATCAAGGAGAGATGACCTCAATTAAAGTATCTTTTAGTGACAAAGAAAATCAGAAAATAAAA
CCTGGAGATACTATTACTTTAACTTTACCAGACGCACTAGTTGGAATGACCGAGAACGATAGTTCACCAC
GAAAAATCAATTTAAATGGTTTAGGGGAAGTTTTTATCTATAAAGATCATGTTGTAGCAACATTTAACGA
AAAAGTTGAATCTTTACATAATGTGAATGGGCATTTTTCTTTCGGGATTAAAACGCTTATCACCAATAGT
TCTCAACCGAATGTGATAGAAACGGATTTCGGAACAGCAACGGCGACTCAACGTTTGACGATTGAAGGAG
TGACTAACACAGAGACTGGCCAAATTGAGCGAGACTATCCGTTTTTTTATAAAGTAGGCGATTTGGCTGG
AGAGTCAAATCAAGTACGTTGGTTTTTAAATGTGAACCTCAATAAATCCGATGTCACAGAAGATATTTCA
ATTGCGGATCGACAAGGAAGTGGTCAACAATTAAATAAAGAGTTTTACATTTGATATTGTGAATGACAA
AAGAAACTAAATATATTTCACTTGCCGAGTTTGAGCAACAAGGTTATGGCAAAATTGACTTCGTAACAGA
TAATGACTTTAACTTACGTTTTTATCGGGATAAAGCACGCTTTACTTCCTTTATCGTCCGTTACACTTCG
ACAATCACAGAAGCAGGCCAACATCAAGCAACATTTGAAAATAGTTATGACATCAATTATCAACTAAACA
ATCAAGACGCAACGAATGAAAAAAATACATCACAGGTTAAAAATGTTTTTGTAGAAGGCGAGCCAAGCGG
CAATCAAAATGTGGAAATGCCAACAGAAGAAAGTCTAGACATTCCTTTAGAGACAATAGATGAATGGGAA
CCAAAGACACCTACTTCGGAACAGGCAACAGAAACAAGTGAAAAGACAGACACAACAGAAACCGCAGAAA
GCAGCCAACCAGAAGTTCATGTCTCACCAACAGAAGAAGAAAATCCAGATGAAGGTGAAACACTAGGCAC
GATTGAGCCAATCATACCTGAAAAACCAAGTGTGACAACTGAAGGACACGACGAAACTGCAGAA
AGCAGCCAACCAGAAGTTCATGTCTCACCAACAGAAGAAGAAAATCCAGATGAAAGTGAAACACTAGGCA
CGATTGAGCCAATCATACCTGAAAAACCAAGTGTGACAACTGAAGAGAACGGCACAACAGAAACCGCAGA
AAGCAGCCAACCAGAAGTTCATGTCTCACCAGCGGAAGAAGAAATCCAGATGAAAGTGAAACGTTAGGT
ACAATTTTACCAATCCTACCTGAAAAACCAAGTGTGACAACTGAAGAGAATGGCACAACGGAAACTGCAG
AAAGCAGCCAACCAGAAGTCCATGTCTCGCCAACGGAAGAAATCCAGATGAAAGTGAAACACTAGG
CACGATTGCACCAATCATACCTGAAAAACCAAGCGTAACAACTGAAGAATGGTATAACGGAAACGGCA
GAAAGCAGCCAGCCAGAAGTTCATGTCTCACCAACAAAGAAATTACTACAACTGAGAAAAAACAGCCAT
CCACAGAAACAACTGTGGAGAAAAATAAAAATGTTACATCAAAAAATCAACCACAAATACTAAACGCTCC
ATTAAATACATTGAAAAATGAAGGAAGCCCACAGTTGGCTCCCCAACTGCTTAGTGAACCAATTCAAAAA
TTAAATGAAGCAAACGGGCAACGAGAACTTCCCAAACAGGCACAACAAAACACCGTTTATGCTAATAG
CAGGAATACTGGCAAGTACATTTGCCGTTTAGGTGTAAGTTATCTACAAATCAGAAAGAATTAA

FIGURE 23

SEQ ID NO. 5 (NCBI Entrez Accession Code: 2F6A_A):

GSARDISSTNVTDLTVSPSKIEDGGKTTVKMTFDDKNGKIQNGDMIKVAWPTSGTVKIEGYSKTVPLTVK
GEQVGQAVITPDGATITFNDKVEKLSDVSGFAEFEVQGRNLTQTNTSDDKVATITSGNKSTNVTVHKSEA
GTSSVFYYKTGDMLPEDTTHVRWFLNINNEKSYVSKDITIKDQIQGGQQLDLSTLNINVTGTHSNYYSGQ
SAITDFEKAFPGSKITVDNTKNTIDVTIPQGYGSYNSFSINYKTKITNEQQKEFVNNSQAWYQEHGKEEV
NGKSFNHTVHNINANAGIEGTVK

SEQ ID NO. 6

MTIEEDSATHIKFSKRDIDGKELAGATMELRDSSGKTISTWISDGQVKDFYLMPGKYTFV
ETAAPDGYEVATAITFTVNEQGQVTVNGKATKGDAHIVMVDA-

SEQ ID NO. 7

ATGACAATTGAAGAAGATAGTGCTACCCATATTAAATTCTCAAAACGTGATATTGACGGCAAAGAGTTAGCTGGTGCAACTATGGA
GTTGCGTGATTCATCTGGTAAAACTATTAGTACATGGATTTCAGATGGACAAGTGAAAGATTTCTACCTGATGCCAGGAAAATATA
CATTTGTCGAAACCGCAGCACCAGACGGTTATGAGGTAGCAACTGCTATTACCTTTACAGTTAATGAGCAAGGTCAGGTTACTGTA
AATGGCAAAGCAACTAAAGGTGACGCTCATATTGTCATGGTTGATGCT<u>TGA</u>

FIGURE 23 (cont.)

SEQUENCE LISTING

<160> NUMBER OF SEQ ID NOS: 38

<210> SEQ ID NO 1
<211> LENGTH: 340
<212> TYPE: PRT
<213> ORGANISM: Streptococcus pyogenes

<400> SEQUENCE: 1

Met Lys Leu Arg His Leu Leu Thr Gly Ala Ala Leu Thr Ser Phe
1               5                   10                  15

Ala Ala Thr Thr Val His Gly Glu Thr Val Val Asn Gly Ala Lys Leu
                20                  25                  30

Thr Val Thr Lys Asn Leu Asp Leu Val Asn Ser Asn Ala Leu Ile Pro
                35                  40                  45

Asn Thr Asp Phe Thr Phe Lys Ile Glu Pro Asp Thr Thr Val Asn Glu
    50                  55                  60

Asp Gly Asn Lys Phe Lys Gly Val Ala Leu Asn Thr Pro Met Thr Lys
65                  70                  75                  80

Val Thr Tyr Thr Asn Ser Asp Lys Gly Gly Ser Asn Thr Lys Thr Ala
                85                  90                  95

Glu Phe Asp Phe Ser Glu Val Thr Phe Glu Lys Pro Gly Val Tyr Tyr
                100                 105                 110

Tyr Lys Val Thr Glu Glu Lys Ile Asp Lys Val Pro Gly Val Ser Tyr
                115                 120                 125

Asp Thr Thr Ser Tyr Thr Val Gln Val His Val Leu Trp Asn Glu Glu
    130                 135                 140

Gln Gln Lys Pro Val Ala Thr Tyr Ile Val Gly Tyr Lys Glu Gly Ser
145                 150                 155                 160

Lys Val Pro Ile Gln Phe Lys Asn Ser Leu Asp Ser Thr Thr Leu Thr
                165                 170                 175

Val Lys Lys Lys Val Ser Gly Thr Gly Gly Asp Arg Ser Lys Asp Phe
                180                 185                 190

Asn Phe Gly Leu Thr Leu Lys Ala Asn Gln Tyr Tyr Lys Ala Ser Glu
                195                 200                 205

Lys Val Met Ile Glu Lys Thr Thr Lys Gly Gly Gln Ala Pro Val Gln
    210                 215                 220

Thr Glu Ala Ser Ile Asp Gln Leu Tyr His Phe Thr Leu Lys Asp Gly
225                 230                 235                 240

Glu Ser Ile Lys Val Thr Asn Leu Pro Val Gly Val Asp Tyr Val Val
                245                 250                 255

Thr Glu Asp Asp Tyr Lys Ser Glu Lys Tyr Thr Thr Asn Val Glu Val
                260                 265                 270

Ser Pro Gln Asp Gly Ala Val Lys Asn Ile Ala Gly Asn Ser Thr Glu
    275                 280                 285

Gln Glu Thr Ser Thr Asp Lys Asp Met Thr Ile Thr Phe Thr Asn Lys
                290                 295                 300

Lys Asp Phe Glu Val Pro Thr Gly Val Ala Met Thr Val Ala Pro Tyr
305                 310                 315                 320

Ile Ala Leu Gly Ile Val Ala Val Gly Gly Ala Leu Tyr Phe Val Lys
                325                 330                 335

Lys Lys Asn Ala
            340

<210> SEQ ID NO 2
<211> LENGTH: 1023

```
<212> TYPE: DNA
<213> ORGANISM: Streptococcus pyogenes

<400> SEQUENCE: 2
atgaaattac gtcacttact attaacggga gcagccctaa ctagttttgc tgctacaaca      60
gttcacgggg agactgttgt aaacggagcc aaactaacag ttacaaaaaa ccttgattta     120
gttaatagca atgcattaat tccaaataca gattttacat ttaaaatcga acctgatact     180
actgtcaacg aagacggaaa taagtttaaa ggtgtagctt tgaacacacc gatgactaaa     240
gtcacttaca ccaattcaga taaaggtgga tcaaatacga aaactgcaga atttgatttt     300
tcagaagtta cttttgaaaa accaggtgtt tattattaca agtaactga ggagaagata      360
gataaagttc ctggtgtttc ttatgataca acatcttaca ctgttcaagt tcatgtcttg     420
tggaatgaag agcaacaaaa accagtagct acttatattg ttggttataa agaaggtagt     480
aaggtgccaa ttcagttcaa aaatagctta gattctacta cattaacggt gaagaaaaaa     540
gtttcaggta ccggtggaga tcgctctaaa gattttaatt ttggtctgac tttaaaagca     600
aatcagtatt ataaggcgtc agaaaaagtc atgattgaga agacaactaa aggtggtcaa     660
gctcctgttc aaacagaggc tagtatagat caactctatc attttacctt gaaagatggt     720
gaatcaatca agtcacaaa tcttccagta ggtgtggatt atgttgtcac tgaagacgat     780
tacaaatcag aaaatatac aaccaacgtg gaagttagtc ctcaagatgg agctgtaaaa     840
aatatcgcag gtaattcaac tgaacaagag acatctactg ataaagatat gaccattact     900
tttacaaata aaaagacttt gaagtgcca acaggagtag caatgactgt ggcaccatat      960
attgctttag gaattgtagc agttggtgga gctctttact ttgttaaaaa gaaaaatgct    1020
taa                                                                  1023
```

<210> SEQ ID NO 3
<211> LENGTH: 674
<212> TYPE: PRT
<213> ORGANISM: Enterococcus faecalis

<400> SEQUENCE: 3

```
Met Thr Lys Ser Val Lys Phe Leu Val Leu Leu Val Met Ile Leu
1               5                   10                  15

Pro Ile Ala Gly Ala Leu Leu Ile Gly Pro Ile Ser Phe Gly Ala Glu
            20                  25                  30

Leu Ser Lys Ser Ser Ile Val Asp Lys Val Glu Leu Asp His Thr Thr
        35                  40                  45

Leu Tyr Gln Gly Glu Met Thr Ser Ile Lys Val Ser Phe Ser Asp Lys
    50                  55                  60

Glu Asn Gln Lys Ile Lys Pro Gly Asp Thr Ile Thr Leu Thr Leu Pro
65                  70                  75                  80

Asp Ala Leu Val Gly Met Thr Glu Asn Asp Ser Ser Pro Arg Lys Ile
                85                  90                  95

Asn Leu Asn Gly Leu Gly Glu Val Phe Ile Tyr Lys Asp His Val Val
            100                 105                 110

Ala Thr Phe Asn Glu Lys Val Glu Ser Leu His Asn Val Asn Gly His
        115                 120                 125

Phe Ser Phe Gly Ile Lys Thr Leu Ile Thr Asn Ser Ser Gln Pro Asn
    130                 135                 140

Val Ile Glu Thr Asp Phe Gly Thr Ala Thr Ala Thr Gln Arg Leu Thr
145                 150                 155                 160
```

```
Ile Glu Gly Val Thr Asn Thr Glu Thr Gly Gln Ile Glu Arg Asp Tyr
                165                 170                 175

Pro Phe Phe Tyr Lys Val Gly Asp Leu Ala Gly Glu Ser Asn Gln Val
                180                 185                 190

Arg Trp Phe Leu Asn Val Asn Leu Asn Lys Ser Asp Val Thr Glu Asp
            195                 200                 205

Ile Ser Ile Ala Asp Arg Gln Gly Ser Gly Gln Gln Leu Asn Lys Glu
            210                 215                 220

Ser Phe Thr Phe Asp Ile Val Asn Asp Lys Glu Thr Lys Tyr Ile Ser
225                 230                 235                 240

Leu Ala Glu Phe Glu Gln Gln Gly Tyr Gly Lys Ile Asp Phe Val Thr
                245                 250                 255

Asp Asn Asp Phe Asn Leu Arg Phe Tyr Arg Asp Lys Ala Arg Phe Thr
                260                 265                 270

Ser Phe Ile Val Arg Tyr Thr Ser Thr Ile Thr Glu Ala Gly Gln His
                275                 280                 285

Gln Ala Thr Phe Glu Asn Ser Tyr Asp Ile Asn Tyr Gln Leu Asn Asn
            290                 295                 300

Gln Asp Ala Thr Asn Glu Lys Asn Thr Ser Gln Val Lys Asn Val Phe
305                 310                 315                 320

Val Glu Gly Glu Ala Ser Gly Asn Gln Asn Val Glu Met Pro Thr Glu
                325                 330                 335

Glu Ser Leu Asp Ile Pro Leu Glu Thr Ile Asp Glu Trp Glu Pro Lys
                340                 345                 350

Thr Pro Thr Ser Glu Gln Ala Thr Glu Thr Ser Glu Lys Thr Asp Thr
            355                 360                 365

Thr Glu Thr Ala Glu Ser Ser Gln Pro Glu Val His Val Ser Pro Thr
370                 375                 380

Glu Glu Glu Asn Pro Asp Glu Gly Glu Thr Leu Gly Thr Ile Glu Pro
385                 390                 395                 400

Ile Ile Pro Glu Lys Pro Ser Val Thr Thr Glu Glu Asn Gly Thr Thr
                405                 410                 415

Glu Thr Ala Glu Ser Ser Gln Pro Glu Val His Val Ser Pro Thr Glu
                420                 425                 430

Glu Glu Asn Pro Asp Glu Ser Glu Thr Leu Gly Thr Ile Glu Pro Ile
            435                 440                 445

Ile Pro Glu Lys Pro Ser Val Thr Thr Glu Glu Asn Gly Thr Thr Glu
            450                 455                 460

Thr Ala Glu Ser Ser Gln Pro Glu Val His Val Ser Pro Ala Glu Glu
465                 470                 475                 480

Glu Asn Pro Asp Glu Ser Glu Thr Leu Gly Thr Ile Leu Pro Ile Leu
                485                 490                 495

Pro Glu Lys Pro Ser Val Thr Thr Glu Glu Asn Gly Thr Thr Glu Thr
                500                 505                 510

Ala Glu Ser Ser Gln Pro Glu Val His Val Ser Pro Thr Glu Glu Glu
                515                 520                 525

Asn Pro Asp Glu Ser Glu Thr Leu Gly Thr Ile Ala Pro Ile Ile Pro
            530                 535                 540

Glu Lys Pro Ser Val Thr Thr Glu Glu Asn Gly Ile Thr Glu Thr Ala
545                 550                 555                 560

Glu Ser Ser Gln Pro Glu Val His Val Ser Pro Thr Lys Glu Ile Thr
                565                 570                 575

Thr Thr Glu Lys Lys Gln Pro Ser Thr Glu Thr Thr Val Glu Lys Asn
```

```
                580             585             590
Lys Asn Val Thr Ser Lys Asn Gln Pro Gln Ile Leu Asn Ala Pro Leu
                    595             600             605

Asn Thr Leu Lys Asn Glu Gly Ser Pro Gln Leu Ala Pro Gln Leu Leu
            610             615             620

Ser Glu Pro Ile Gln Lys Leu Asn Glu Ala Asn Gly Gln Arg Glu Leu
625             630             635             640

Pro Lys Thr Gly Thr Thr Lys Thr Pro Phe Met Leu Ile Ala Gly Ile
                645             650             655

Leu Ala Ser Thr Phe Ala Val Leu Gly Val Ser Tyr Leu Gln Ile Arg
                660             665             670

Lys Asn

<210> SEQ ID NO 4
<211> LENGTH: 2025
<212> TYPE: DNA
<213> ORGANISM: Enterococcus faecalis

<400> SEQUENCE: 4
```

| | | | | | |
|---|---|---|---|---|---|
| atgacaaaaa | gtgtaaaatt | tttagtgtta | ctgttggtaa | tgattctacc | aattgcgggg | 60 |
| gcgttattga | ttggtccaat | tcgtttggc | gccgaattga | gcaaaagttc | aatcgttgac | 120 |
| aaagtagaat | tagatcacac | tactttatat | caaggagaga | tgacctcaat | taaagtatct | 180 |
| tttagtgaca | agaaaatca | gaaataaaa | cctggagata | ctattacttt | aactttacca | 240 |
| gacgcactag | ttggaatgac | cgagaacgat | agttccacca | gaaaaatcaa | tttaaatggt | 300 |
| ttaggggaag | ttttatcta | taaagatcat | gttgtagcaa | catttaacga | aaaagttgaa | 360 |
| tctttacata | atgtgaatgg | gcattttttct | ttcgggatta | aaacgcttat | caccaatagt | 420 |
| tctcaaccga | atgtgataga | aacggatttc | ggaacagcaa | cggcgactca | acgtttgacg | 480 |
| attgaaggag | tgactaacac | agagactggc | caaattgagc | gagactatcc | gtttttttat | 540 |
| aaagtaggcg | atttggctgg | agagtcaaat | caagtacgtt | ggttttaaa | tgtgaacctc | 600 |
| aataaatccg | atgtcacaga | agatatttca | attgcggatc | gacaaggaag | tggtcaacaa | 660 |
| ttaaataaag | agagttttac | atttgatatt | gtgaatgaca | agaaactaa | atatatttca | 720 |
| cttgccgagt | ttgagcaaca | aggttatggc | aaaattgact | cgtaacaga | taatgacttt | 780 |
| aacttacgtt | tttatcggga | taagcacgc | tttacttcct | ttatcgtccg | ttacacttcg | 840 |
| acaatcacag | aagcaggcca | acatcaagca | acatttgaaa | atagttatga | catcaattat | 900 |
| caactaaaca | atcaagacgc | aacgaatgaa | aaaatacat | cacaggttaa | aaatgttttt | 960 |
| gtagaaggcg | aggcaagcgg | caatcaaaat | gtggaaatgc | aacagaaga | aagtctagac | 1020 |
| attccttag | agacaataga | tgaatgggaa | ccaaagacac | ctacttcgga | acaggcaaca | 1080 |
| gaaacaagtg | aaaagacaga | cacaacagaa | accgcagaaa | gcagccaacc | agaagttcat | 1140 |
| gtctcaccaa | cagaagaaga | aaatccagat | gaaggtgaaa | cactaggcac | gattgagcca | 1200 |
| atcatacctg | aaaaccaag | tgtgacaact | gaagagaatg | gcacgacaga | aactgcagaa | 1260 |
| agcagccaac | cagaagttca | tgtctcacca | acagaagaag | aaaatccaga | tgaaagtgaa | 1320 |
| acactaggca | cgattgagcc | aatcatacct | gaaaaaccaa | gtgtgacaac | tgaagagaac | 1380 |
| ggcacaacag | aaaccgcaga | aagcagccaa | ccagaagttc | atgtctcacc | agcggaagaa | 1440 |
| gaaaatccag | atgaaagtga | aacgttaggt | acaattttac | caatcctacc | tgaaaaacca | 1500 |
| agtgtgacaa | ctgaagagaa | tggcacaacg | gaaactgcga | aaagcagtca | accagaagtc | 1560 |

-continued

```
catgtgtcgc caacggaaga agaaaatcca gatgaaagtg aaacactagg cacgattgca    1620
ccaatcatac ctgaaaaacc aagcgtaaca actgaagaga atggtataac ggaaacggca    1680
gaaagcagcc agccagaagt tcatgtctca ccaacaaaag aaattactac aactgagaaa    1740
aaacagccat ccacagaaac aactgtggag aaaaataaaa atgttacatc aaaaaatcaa    1800
ccacaaatac taaacgctcc attaaataca ttgaaaaatg aaggaagccc acagttggct    1860
ccccaactgc ttagtgaacc aattcaaaaa ttaaatgaag caaacgggca acgagaactt    1920
cccaaaacag gcacaacaaa acaccgtttt atgctaatag caggaatact ggcaagtaca    1980
tttgccgttt taggtgtaag ttatctacaa atcagaaaga attaa    2025
```

<210> SEQ ID NO 5
<211> LENGTH: 303
<212> TYPE: PRT
<213> ORGANISM: Staphylococcus aureus

<400> SEQUENCE: 5

```
Gly Ser Ala Arg Asp Ile Ser Ser Thr Asn Val Thr Asp Leu Thr Val
1               5                   10                  15

Ser Pro Ser Lys Ile Glu Asp Gly Gly Lys Thr Thr Val Lys Met Thr
            20                  25                  30

Phe Asp Asp Lys Asn Gly Lys Ile Gln Asn Gly Asp Met Ile Lys Val
        35                  40                  45

Ala Trp Pro Thr Ser Gly Thr Val Lys Ile Glu Gly Tyr Ser Lys Thr
    50                  55                  60

Val Pro Leu Thr Val Lys Gly Glu Gln Val Gly Gln Ala Val Ile Thr
65                  70                  75                  80

Pro Asp Gly Ala Thr Ile Thr Phe Asn Asp Lys Val Glu Lys Leu Ser
                85                  90                  95

Asp Val Ser Gly Phe Ala Glu Phe Glu Val Gln Gly Arg Asn Leu Thr
            100                 105                 110

Gln Thr Asn Thr Ser Asp Asp Lys Val Ala Thr Ile Thr Ser Gly Asn
        115                 120                 125

Lys Ser Thr Asn Val Thr Val His Lys Ser Glu Ala Gly Thr Ser Ser
    130                 135                 140

Val Phe Tyr Tyr Lys Thr Gly Asp Met Leu Pro Glu Asp Thr Thr His
145                 150                 155                 160

Val Arg Trp Phe Leu Asn Ile Asn Asn Glu Lys Ser Tyr Val Ser Lys
                165                 170                 175

Asp Ile Thr Ile Lys Asp Gln Ile Gln Gly Gly Gln Gln Leu Asp Leu
            180                 185                 190

Ser Thr Leu Asn Ile Asn Val Thr Gly Thr His Ser Asn Tyr Tyr Ser
        195                 200                 205

Gly Gln Ser Ala Ile Thr Asp Phe Glu Lys Ala Phe Pro Gly Ser Lys
    210                 215                 220

Ile Thr Val Asp Asn Thr Lys Asn Thr Ile Asp Val Thr Ile Pro Gln
225                 230                 235                 240

Gly Tyr Gly Ser Tyr Asn Ser Phe Ser Ile Asn Tyr Lys Thr Lys Ile
                245                 250                 255

Thr Asn Glu Gln Gln Lys Glu Phe Val Asn Asn Ser Gln Ala Trp Tyr
            260                 265                 270

Gln Glu His Gly Lys Glu Glu Val Asn Gly Lys Ser Phe Asn His Thr
        275                 280                 285

Val His Asn Ile Asn Ala Asn Ala Gly Ile Glu Gly Thr Val Lys
    290                 295                 300
```

<210> SEQ ID NO 6
<211> LENGTH: 102
<212> TYPE: PRT
<213> ORGANISM: Streptococcus pyogenes

<400> SEQUENCE: 6

Met Thr Ile Glu Glu Asp Ser Ala Thr His Ile Lys Phe Ser Lys Arg
1               5                   10                  15
Asp Ile Asp Gly Lys Glu Leu Ala Gly Ala Thr Met Glu Leu Arg Asp
            20                  25                  30
Ser Ser Gly Lys Thr Ile Ser Thr Trp Ile Ser Asp Gly Gln Val Lys
        35                  40                  45
Asp Phe Tyr Leu Met Pro Gly Lys Tyr Thr Phe Val Glu Thr Ala Ala
    50                  55                  60
Pro Asp Gly Tyr Glu Val Ala Thr Ala Ile Thr Phe Thr Val Asn Glu
65                  70                  75                  80
Gln Gly Gln Val Thr Val Asn Gly Lys Ala Thr Lys Gly Asp Ala His
                85                  90                  95
Ile Val Met Val Asp Ala
            100

<210> SEQ ID NO 7
<211> LENGTH: 309
<212> TYPE: DNA
<213> ORGANISM: Streptococcus pyogenes

<400> SEQUENCE: 7
atgacaattg aagaagatag tgctacccat attaaattct caaaacgtga tattgacggc    60
aaagagttag ctggtgcaac tatggagttg cgtgattcat ctggtaaaac tattagtaca   120
tggatttcag atggacaagt gaaagatttc tacctgatgc aggaaaata cacatttgtc   180 gaaaccgcag caccagacgg ttatgaggta gcaactgcta ttacctttac agttaatgag   240
caaggtcagg ttactgtaaa tggcaaagca actaaaggtg acgctcatat tgtcatggtt   300
gatgcttga                                                          309

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
ggggcatatg gctacaacag ttcacggg                                      28

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
ggggaagctt ttattcaaag tctttttttat ttg                               33

<210> SEQ ID NO 10
<211> LENGTH: 31
<212> TYPE: DNA

```
<213> ORGANISM: Artificial Sequence
<220> FEATURE:
<223> OTHER INFORMATION: Primer

<400> SEQUENCE: 10
ggggcatatg ggaactgata aagatatgac c                            31

<210> SEQ ID NO 11
<211> LENGTH: 38
<212> TYPE: DNA
<213> ORGANISM: Artificial Sequence
<220> FEATURE:
<223> OTHER INFORMATION: Primer

<400> SEQUENCE: 11
accactttca ccactacctt caaagtcttt tttatttg                     38

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
aaggtagtgg tgaaagtggt aaaatcgaag aaggtaaa                     38

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
ggggaagctt ttacgagctc gaattagtct g                            31

<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14
tttacaaata aaaagacgc tgaaggtagt ggtgaaag                      38

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
gggcatatgg gaaccattac ttttacaaat                              30

<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16
ggggaagctt ttacgagctc gaattagtct g                            31
```

<210> SEQ ID NO 17
<211> LENGTH: 71
<212> TYPE: DNA
<213> ORGANISM: Artificial Sequence
<220> FEATURE:
<223> OTHER INFORMATION: Primer

<400> SEQUENCE: 17
acaagagaca tctactgata aagatatgac catttagttt acaaataaaa aagactttga    60
ataaaagctt g                                                        71

<210> SEQ ID NO 18
<211> LENGTH: 44
<212> TYPE: DNA
<213> ORGANISM: Artificial Sequence
<220> FEATURE:
<223> OTHER INFORMATION: Primer

<400> SEQUENCE: 18
tctactacat taacggtgaa ggcaaaagtt tcaggtaccg gtgg                     44

<210> SEQ ID NO 19
<211> LENGTH: 71
<212> TYPE: DNA
<213> ORGANISM: Artificial Sequence
<220> FEATURE:
<223> OTHER INFORMATION: Primer

<400> SEQUENCE: 19
acaagagaca tctactgata aagatatgac catttagttt acaaataaaa aagactttga    60
ataaaagctt g                                                        71

<210> SEQ ID NO 20
<211> LENGTH: 63
<212> TYPE: DNA
<213> ORGANISM: Artificial Sequence
<220> FEATURE:
<223> OTHER INFORMATION: Primer

<400> SEQUENCE: 20
gcaggtaatt caactgaaca agagacatct taggataaag atatgaccat tacttttaca    60
aat                                                                 63

<210> SEQ ID NO 21
<211> LENGTH: 69
<212> TYPE: DNA
<213> ORGANISM: Artificial Sequence
<220> FEATURE:
<223> OTHER INFORMATION: Primer

<400> SEQUENCE: 21
actgaacaag agacatctac tgataaagat atgtagatta cttttacaaa taaaaagac    60 tttgaagtg                                                           69

<210> SEQ ID NO 22
<211> LENGTH: 69
<212> TYPE: DNA
<213> ORGANISM: Artificial Sequence
<220> FEATURE:
<223> OTHER INFORMATION: Primer

<400> SEQUENCE: 22

```
gaacaagaga catctactga taaagatatg acctagactt ttacaaataa aaaagacttt    60
gaataaaag                                                           69
```

<210> SEQ ID NO 23
<211> LENGTH: 65
<212> TYPE: DNA
<213> ORGANISM: Artificial Sequence
<220> FEATURE:
<223> OTHER INFORMATION: Primer

<400> SEQUENCE: 23

```
caagagacat ctactgataa agatatgacc attacttaga caaataaaaa agactttgaa    60
taaaa                                                                65
```

<210> SEQ ID NO 24
<211> LENGTH: 50
<212> TYPE: DNA
<213> ORGANISM: Artificial Sequence
<220> FEATURE:
<223> OTHER INFORMATION: Primer

<400> SEQUENCE: 24

```
ctaattcgag ctcgggttcg ggtgaaagtg gtgctacaac agttcacggg              50
```

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25

```
ggggaagctt ttatgcattg ctattaacta aatc                               34
```

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26

```
caagcatatg aaaatcgaag aag                                           23
```

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27

```
cgaacccgag ctcgaattag tctg                                          24
```

<210> SEQ ID NO 28
<211> LENGTH: 31
<212> TYPE: DNA
<213> ORGANISM: Artificial Sequence
<220> FEATURE:
<223> OTHER INFORMATION: Primer

<400> SEQUENCE: 28

```
ggggcatatg ggattaattc caaatacaga t                                  31
```

<210> SEQ ID NO 29
<211> LENGTH: 60
<212> TYPE: DNA
<213> ORGANISM: Artificial Sequence
<220> FEATURE:
<223> OTHER INFORMATION: Primer

<400> SEQUENCE: 29
ggggaagctt ctagtgatgg tgatggtgat gtcctgatcc ttcaaagtct tttttatttg    60

<210> SEQ ID NO 30
<211> LENGTH: 49
<212> TYPE: DNA
<213> ORGANISM: Artificial Sequence
<220> FEATURE:
<223> OTHER INFORMATION: Primer

<400> SEQUENCE: 30
gtgtttatta ttacaaagta actgcggaga agatagataa agttcctgg                49

<210> SEQ ID NO 31
<211> LENGTH: 90
<212> TYPE: DNA
<213> ORGANISM: Artificial Sequence
<220> FEATURE:
<223> OTHER INFORMATION: Primer

<400> SEQUENCE: 31
gacagatctg gcggcactga taaagatatg accattactt ttacaaataa aaagactttg    60
gaaggtagtg gtatggtgag caagggcgag                                     90

<210> SEQ ID NO 32
<211> LENGTH: 40
<212> TYPE: DNA
<213> ORGANISM: Artificial Sequence
<220> FEATURE:
<223> OTHER INFORMATION: Primer

<400> SEQUENCE: 32
actctcggca tggacgagct atacaagcgg ccgcggggag                          40

<210> SEQ ID NO 33
<211> LENGTH: 16
<212> TYPE: PRT
<213> ORGANISM: Artificial sequence
<220> FEATURE:
<223> OTHER INFORMATION: isopeptag-MBP construct

<400> SEQUENCE: 33

Thr Asp Lys Asp Met Thr Ile Thr Phe Thr Asn Lys Lys Asp Ala Glu
1               5                   10                  15

<210> SEQ ID NO 34
<211> LENGTH: 11
<213> ORGANISM: Artificial sequence
<220> FEATURE:
<223> OTHER INFORMATION: isopeptag-MBP -5

<400> SEQUENCE: 34

Thr Ile Thr Phe Thr Asn Lys Lys Asp Phe Glu
1               5                   10

<210> SEQ ID NO 35
<211> LENGTH: 7
<212> TYPE: PRT

```
<213> ORGANISM: Artificial sequence
<220> FEATURE:
<223> OTHER INFORMATION: pilin-C -2 construct

<400> SEQUENCE: 35

Thr Ser Thr Asp Lys Asp Met
1               5

<210> SEQ ID NO 36
<211> LENGTH: 8
<212> TYPE: PRT
<213> ORGANISM: Artificial sequence
<220> FEATURE:
<223> OTHER INFORMATION: Pilin-C -1 construct

<400> SEQUENCE: 36

Thr Ser Thr Asp Lys Asp Met Thr
1               5

<210> SEQ ID NO 37
<211> LENGTH: 9
<212> TYPE: PRT
<213> ORGANISM: Artificial sequence
<220> FEATURE:
<223> OTHER INFORMATION: Pilin-C construct

<400> SEQUENCE: 37

Thr Ser Thr Asp Lys Asp Met Thr Ile
1               5

<210> SEQ ID NO 38
<211> LENGTH: 10
<212> TYPE: PRT
<213> ORGANISM: Artificial sequence
<220> FEATURE:
<223> OTHER INFORMATION: Pilin-C +1 construct

<400> SEQUENCE: 38

Thr Ser Thr Asp Lys Asp Met Thr Ile Thr
1               5                   10
```

PEPTIDE TAG SYSTEM THAT SPONTANEOUSLY FORM AN IRREVERSIBLE LINK TO PROTEIN PARTNERS VIA ISOPEPTIDE BONDS

CROSS-REFERENCE TO RELATED APPLICATIONS

This application is a divisional of U.S. application Ser. No. 13/578,070, filed on Nov. 1, 2012, which is a is a 371 of PCT/GB2011/000188, filed Feb. 11, 2011, which claims the benefit of priority to GB application No. 1002362.0, filed on Feb. 11, 2010, under the provisions of 35 U.S.C. 119 and the International Convention for the protection of Industrial Property, which are incorporated herein by reference.

BACKGROUND

The use of peptides and peptide-like molecules as tags for attaching to proteins and other entities is an important tool in molecular biology. Such peptide tags can allow the detection, purification and analysis of a particular protein or entity or can be used for the specific targeting of the tagged protein or entity. Thus, peptide tags, which may be attached to a protein of interest using recombinant DNA methods (e.g. by operably linking the nucleotide sequence encoding the peptide tag with the gene encoding the protein of interest and expressing the protein product), usually have the ability to bind to a binding partner. This binding may allow the detection of the protein of interest if the binding partner is detectable, e.g. is an antibody or is conjugated to a detectable entity, or can allow purification of the protein of interest if the binding partner is, for example, immobilised to a solid support. Thus, the use of peptide tags which are capable of associating with a binding partner can provide a means for manipulating or analysing a target protein or entity; this analysis can be used to determine the size, abundance, location in the cell or organism, and the interactions of the tagged protein.

There are a number of different peptide tag systems which are known in the art and which are available commercially, for example, c-myc, FLAG, HA, His6, T7-Tag, Strep-Tag, Avi-Tag to name a few. As indicated above, such peptide tag systems are widely used for detecting, characterising and purifying proteins, where the use of a peptide tag may for example abrogate the need to develop an antibody to the protein of interest, which is a time-consuming and expensive process that is not always successful. The small size of the peptide tag (usually 5-15 amino acids in length) generally has no effect on the biological function of the protein of interest to which it is attached. However, one major problem with the use of peptide tags of the art is the instability of their interactions with their binding partners, with affinity often micromolar and rarely better than nanomolar, relating to the limited accessible surface area and the intrinsic flexibility of the peptides. The peptide flexibility places a large entropic cost on forming a well defined binding interaction. There is therefore a lack of peptide tag/binding partner systems in the art which provide high affinity or irreversible binding and which would be useful to improve the sensitivity of protein detection, the efficiency and yield of protein purification and to provide a rigid link to hold together proteins which are subject to high forces.

SUMMARY

The present invention addresses the need for peptide tag/binding partner pairs with stable or irreversible interactions by adapting a feature of amino acid chemistry, namely the spontaneous formation of isopeptide bonds (which may for example occur between a lysine and an asparagine residue in an appropriate environment).

DETAILED DESCRIPTION

Isopeptide bonds are amide bonds formed between carboxyl/carboxamide and amino groups, where at least one of the carboxyl or amino groups is outside of the protein main-chain (the backbone of the protein). Such bonds are chemically irreversible under biological conditions and they are resistant to most proteases. Bond formation can be enzyme catalysed, for example by transglutaminase enzymes, where the resulting bonds function to stabilise extracellular matrix structures or to strengthen blood clots, or isopeptide bonds may form spontaneously as has been identified in HK97 bacteriophage capsid formation and Gram-positive bacterial pili. Spontaneous isopeptide bond formation has been proposed to occur after protein folding, through nucleophilic attack of the ε-amino group from a lysine on the Cγ group of an asparagine, promoted by a nearby glutamate.

The present invention thus uses proteins which are capable of spontaneous isopeptide bond formation, to develop peptide tag/binding partner pairs which covalently bind to each other and which hence provide irreversible interactions. In this respect, proteins which are capable of spontaneous isopeptide bond formation may be expressed as separate fragments, to give a peptide tag and a binding partner for the peptide tag, where the two fragments are capable of covalently reconstituting by isopeptide bond formation. This covalent reaction through an isopeptide bond makes the peptide-protein interaction stable under conditions where non-covalent interactions would rapidly dissociate—over long times (e.g. weeks), at high temperature (to at least 95° C.), at high force, or with harsh chemical treatment (e.g. pH 2-11, organic solvent, detergents or denaturants). As discussed in detail below, the peptide tag may comprise one or more residues involved in the isopeptide bond in the original protein and the binding partner may comprise the other residue(s) involved in the isopeptide bond in the original protein. In this way, it is possible to use a peptide tag developed from a protein capable of isopeptide bond formation to label a protein of interest and to detect or purify the protein of interest by the binding of the peptide tag to a binding partner developed from the isopeptide protein.

Thus, proteins capable of isopeptide bonding have been used to develop peptide tag/binding partner pairs since splitting of the protein may form a tag and a binding partner which can reconstitute through covalent bonding and thus can provide a peptide tag/binding partner pair with irreversible interactions. Hence, the coding sequence for the protein may be cleaved to form fragments which encode the peptide tag and binding partner pair. Thus as discussed in detail below, the peptide tag and/or binding partner may be designed using the initial protein sequence but may be produced using other methods such as recombinant expression. Further, other peptide tags which bind to the binding partner as designed using the isopeptide protein may be identified by screening a peptide library. Similarly a library of binding partners may be screened for optimal properties of isopeptide bond formation with the peptide tag. Such a use of spontaneous isopeptide bonding for the development of peptide tag and binding partner pairs has not previously been suggested in the art. In a first embodiment, the present invention therefore provides a use of a protein capable of spontaneously forming an isopeptide bond for the development/production of a peptide tag and binding partner pair wherein the peptide tag and binding partner are capable of spontaneously binding to each other by forming an isopeptide bond.

Therefore, as discussed briefly above, it is possible to produce or develop a peptide tag and binding partner pair which are able to reconstitute and covalently bind to each other from a protein which is able to spontaneously form an isopeptide bond (alternatively referred to herein as "an isopeptide protein").

Thus, the peptide tag and binding partner pair may comprise fragments of an isopeptide protein or sequences which are homologous to such fragments e.g. which have at least 50, 60, 70, 80 or 90% identity thereto, which are able to covalently bind to one another e.g. by forming an isopeptide bond. Alternatively, a binding partner may be developed from an isopeptide protein and a corresponding peptide tag which covalently binds thereto may be identified by screening a peptide library as discussed in greater detail below. The peptide tag and binding partner fragments preferably each comprise an amino acid residue from the isopeptide protein which was involved in the spontaneously formed isopeptide bond (referred to herein as a "reactive" residue). Thus, preferably neither the peptide tag nor the binding partner comprise both reactive residues involved in the isopeptide bond. Each isopeptide bond generally forms between 2 reactive residues and thus, preferably a peptide tag and binding partner pair which covalently bind to each other, each comprise one of the reactive residues involved in the isopeptide bond. In this way, the peptide tag and binding partner fragments can bind together by spontaneously forming an isopeptide bond between the reactive residue present in the peptide tag and the reactive residue present in the binding partner. The amino acids usually involved in forming a spontaneous isopeptide bond are lysine and asparagine/aspartate and thus, preferably, the peptide tag will comprise one of these residues and the binding partner will comprise the other residue. Thus, if the peptide tag comprises the reactive lysine residue which is involved in the isopeptide bond in the isopeptide protein, then the binding partner may comprise the reactive asparagine or aspartate residue. Alternatively viewed, if the peptide tag comprises the reactive asparagine or aspartate residue which is involved in the isopeptide bond in the isopeptide protein, then the binding partner may comprise the reactive lysine residue. As discussed above, preferably neither the peptide tag nor the binding partner will comprise both the lysine and asparagine/aspartate reactive residues.

The term "isopeptide bond" as used herein, refers to an amide bond between a carboxyl group and an amino group at least one of which is not derived from a protein main chain or alternatively viewed is not part of the protein backbone. An isopeptide bond may form within a single protein or may occur between two peptides or a peptide and a protein. Thus, an isopeptide may form intramolecularly within a single protein or intermolecularly i.e. between two peptide/protein molecules. Typically, an isopeptide bond may occur between a lysine residue and an asparagine, aspartic acid, glutamine, or glutamic acid residue or the terminal carboxyl group of the protein or peptide chain or may occur between the alpha-amino terminus of the protein or peptide chain and an asparagine, aspartic acid, glutamine or glutamic acid. Each residue of the pair involved in the isopeptide bond is referred to herein as a reactive residue. Thus, an isopeptide bond may form between a lysine residue and an asparagine residue or between a lysine residue and an aspartic acid residue. Particularly, isopeptide bonds can occur between the side chain amine of lysine and carboxamide group of asparagine.

Distances between residues involved in an isopeptide bond are measured from particular C atoms within the residue. Thus, when lysine is involved in the isopeptide bond, the distance is measured from the C-epsilon atom of the lysine; when the aspartic acid is involved in the isopeptide bond, the distance is measured from the C-gamma atom of the aspartic acid; when asparagine is involved in the isopeptide bond, the distance is measured from the C-gamma atom of the asparagine and when glutamic acid is involved in the isopeptide bond, the distance is measured from the C-delta atom of glutamic acid. These atoms (from which distances are calculated) of the reactive residues involved in the isopeptide bond are referred to herein as "relevant atoms".

Typically, in order for an isopeptide bond to form, the reactive residues e.g. the reactive lysine and asparagine residues (and particularly the relevant atoms thereof; for lysine the C-epsilon atom and for asparagine the C-gamma atom) should be positioned in close proximity to one another in space e.g. in the folded isopeptide protein. Thus, particularly, the reactive residues e.g. the lysine and asparagine (and particularly the relevant atoms thereof) are within 4 Angstrom of each other in the folded protein and may be within 3.8, 3.6, 3.4, 3.2, 3.0, 2.8, 2.6, 2.4, 2.2, 2.0, 1.8 or 1.6 Angstrom of each other. Particularly, the reactive residues (and more particularly their relevant atoms) may be within 1.81, 2.63 or 2.60 Angstrom of each other.

The term "spontaneous" as used herein refers to a bond e.g. an isopeptide or covalent bond which can form in a protein or between peptides or proteins (e.g. between 2 peptides or a peptide and a protein) without any other agent (e.g. an enzyme catalyst) being present and/or without chemical modification of the protein or peptide e.g. without native chemical ligation or chemical coupling using 1-ethyl-3-(3-dimethylaminopropyl) carbodiimide (EDC). Thus, native chemical ligation to modify a peptide or protein to have a C-terminal thioester is not carried out.

Thus, a spontaneous isopeptide bond can form when a protein is isolated on its own or a covalent or isopeptide bond can form between two peptides or a peptide and a protein when in isolation or without chemical modification. A spontaneous isopeptide or covalent bond may therefore form of its own accord in the absence of enzymes or other exogenous substances or without chemical modification. Particularly however, a spontaneous isopeptide or covalent bond may require the presence of a glutamic acid or an aspartic acid residue in the protein or in one of the peptides/proteins involved in the bond to allow formation of the bond in a proximity induced manner.

A spontaneous isopeptide or covalent bond may form almost immediately after the production of a protein or after contact between a peptide tag and binding partner e.g. within 1, 2, 3, 4, 5, 10, 15, 20, 25 or 30 minutes, or within 1, 2, 4, 8, 12, 16, 20 or 24 hours. The bond may form in phosphate-buffered saline (PBS) at pH 7.0 and at 25° C.

Thus, "a protein capable of spontaneously forming an isopeptide bond" (also referred to herein as "an isopeptide protein"), is one which may form an isopeptide bond as defined above, in the absence of enzymes or other substances and/or without chemical modification, within its protein chain i.e. intramolecularly. The two reactive residues for forming the isopeptide bond are therefore comprised within a single protein chain. Thus, proteins which only form isopeptide bonds intermolecularly i.e. with other peptide or protein chains or units are not considered to be isopeptide proteins as used in the present invention. Particularly, the HK97 capsid subunits which have intermolecular isopeptide bonds are excluded. Generally isopeptide proteins may comprise a glutamic acid or aspartic acid residue in close proximity to the two other reactive amino acid residues e.g. to lysine and asparagine, which are involved in the formation of the isopeptide bond. Particularly, the C-delta atom of the glutamic acid or the C-gamma atom of the aspartic acid residue may be within 5.5 Angstrom from a reactive asparagine residue e.g. from the C-gamma atom of a reactive asparagine residue (or aspartic acid, glutamic acid, glutamine or terminal carboxyl), involved in the isopeptide bond, in the folded protein structure. For example, the glutamic acid (e.g. the C-delta atom thereof) may be within 5.4, 5.2, 5.0, 4.8, 4.6, 4.4, 4.2, 4.0, 3.8, 3.6, 3.4, 3.2 or 3.0 Angstrom from the reactive asparagine residue e.g. the C-gamma atom thereof (or aspartic acid C-gamma, glutamic acid C-delta, glutamine C-delta or terminal carboxyl carbon) in the isopeptide bond. Particularly, the glutamic acid residue e.g. the C-delta atom thereof may be 4.99, 3.84 or 3.73 Angstrom from the asparagine residue e.g. the C-gamma atom thereof.

Further, the glutamic acid residue e.g. the C-delta atom thereof may be within 6.5 Angstrom of a reactive lysine residue e.g. the C-epsilon atom thereof, involved in the isopeptide bond, for example within 6.3, 6.1, 5.9, 5.7, 5.5, 5.3, 5.1, 4.9, 4.7, 4.5, 4.3 or 4.1 Angstrom. Particularly, the glutamic acid residue e.g. the C-delta atom thereof may be 6.07, 4.80 or 4.42 Angstrom from a reactive lysine e.g. the C-epsilon atom thereof.

The glutamic acid residue (or aspartic acid residue) may help induce the formation of the isopeptide bond as discussed previously.

Proteins capable of spontaneously forming an isopeptide bond may be capable of forming at least one such bond and may comprise more than one isopeptide bond, for example 2, 3, 4, 5, 6, 7, 8, 9, 10 or more. If more than one spontaneously formed isopeptide bond is present within a protein, then it may be possible to develop several different peptide tag and binding partner pairs from such a protein, as discussed in detail further below. However, it is preferred in the present invention to develop a peptide tag and binding partner pair from an isopeptide protein which comprises a single or only two isopeptide bond.

Examples of known proteins capable of spontaneously forming one or more isopeptide bonds include Spy0128 (Kang et al, Science, 2007, 318(5856), 1625-8), Spy0125 (Pointon et al, J. Biol. Chem., 2010, 285(44), 33858-66) and FbaB (Oke et al, J. Struct Funct Genomics, 2010, 11(2), 167-80) from Streptococcus pyogenes, Cna of Staphylococcus aureus (Kang et al, Science, 2007, 318 (5856), 1625-8), the ACE19 protein of Enterococcus faecalis (Kang et al, Science, 2007, 318(5856), 1625-8), the BcpA pilin from Bacillus cereus (Budzik et al, PNAS USA, 2007, 106(47), 19992-7), the minor pilin GBS52 from Streptococcus agalactiae (Kang et al, Science, 2007, 318(5856), 1625-8), SpaA from Corynebacterium diphtheriae (Kang et al, PNAS USA, 2009, 106(40), 16967-71), SpaP from Streptococcus mutans (Nylander et al, Acta Crystallogr Sect F Struct Biol Cryst Commum., 2011, 67(Pt1), 23-6), RrgA (Izore et al, Structure, 2010, 18(1), 106-15), RrgB (El Mortaji et al, J. Biol. Chem., 2010, 285(16), 12405-15) and RrgC (El Mortaji et al, J. Biol. Chem., 2010, 285(16), 12405-15) from Streptococcus pneumoniae, SspB from Streptococcus gordonii (Forsgren et al, J Mol Biol, 2010, 397(3), 740-51). As discussed above, any of these proteins may hence be used in the present invention to develop a peptide tag/binding partner pair.

Thus, once an isopeptide protein has been identified by bioinformatic sequence analysis or mass spectrometry or structure determination by X-ray crystallography or NMR, and the positions of any isopeptide bonds therein determined, a peptide tag and binding partner of the present invention can be designed, so that each of the peptide tag and binding partner comprise a reactive residue from one of the isopeptide bonds which occurs in the isopeptide protein. Particularly, the reactive residue positioned nearest to a terminus of the isopeptide protein may preferably be comprised in the peptide tag. As discussed below, other modifications may be desired to improve the peptide tag or binding partner.

The major pilin protein Spy0128 has an amino acid sequence as set out in SEQ ID NO. 1 and is encoded by a nucleotide sequence as set out in SEQ ID NO. 2 (see FIG. 9), where two isopeptide bonds are formed in the protein. One isopeptide bond is formed between lysine at position 179 in SEQ ID NO. 1 and asparagine at position 303 in SEQ ID NO. 1 (the reactive residues). The glutamic acid residue which induces the spontaneous isopeptide bond is found at position 258 in SEQ ID NO. 1. Thus, a peptide tag developed from this isopeptide bond in this protein will preferably comprise the reactive asparagine of position 303 and the binding partner may comprise a fragment comprising the reactive lysine at position 179.

Another isopeptide bond in the major pilin protein Spy0128 occurs between the lysine residue at position 36 of SEQ ID NO. 1 and the asparagine residue at position 168 of SEQ ID NO. 1. The glutamic acid residue which induces isopeptide formation is found at position 117 in SEQ ID NO. 1. A peptide tag developed from this isopeptide bond may preferably comprise the reactive lysine residue at position 36 and the binding partner may comprise a fragment of the protein comprising the reactive asparagine at position 168.

ACE19, a domain of an adhesin protein from E. faecalis, as discussed above, also spontaneously forms an isopeptide bond. This domain is substantially smaller than the major pilin protein and its single isopeptide bond occurs at an edge n-strand. ACE19 has an amino acid sequence as set forth in SEQ ID NO. 3 and is encoded by a nucleotide sequence as set forth in SEQ ID NO. 4 (See FIG. 9).

The isopeptide bond occurs between a lysine residue at position 181 of SEQ ID NO. 3 and an asparagine residue at position 294 of SEQ ID NO. 3. The bond is induced by an aspartic acid residue at position 213 in SEQ ID NO. 3. Thus, in this case, a peptide tag developed may preferably comprise the reactive asparagine residue at position 294 and the binding partner may comprise a fragment of the protein comprising the reactive lysine residue at position 181.

The collagen binding domain from S. aureus which has an amino acid sequence set out in SEQ ID NO. 5, comprises one spontaneously formed isopeptide bond. The isopeptide bond occurs between lysine at position 149 of SEQ ID NO. 5 and asparagine at position 266 of SEQ ID NO. 5. The aspartic acid residue which induces the isopeptide bond is at position 182 of SEQ ID NO. 5. Again, the peptide tag developed from this protein may comprise a fragment of the protein comprising the asparagine at residue 266 and the binding partner may comprise a fragment of the protein comprising the lysine at position 149.

FbaB from Streptococcus pyogenes comprises a domain, CnaB2, which has an amino acid sequence set out in SEQ ID NO. 6, is encoded by the nucleotide sequence set out in SEQ ID NO.7 and which comprises one spontaneously formed isopeptide bond. The isopeptide bond in the CnaB2 domain forms between a lysine at position 15 of SEQ ID NO. 6 (position 470 in FbaB sequence) and an aspartic acid residue at position 101 of SEQ ID NO. 6 (position 556 in FbaB sequence) (NMR spectroscopic and theoretical analysis of a spontaneously formed Lys-Asp isopeptide bond; Hagan R M, Björnsson R, McMahon S A, Schomburg B, Braithwaite V, Buhl M, Naismith J H, Schwarz-Linek U. Angew Chem Int Ed Engl. 2010 Nov. 2; 49(45):8421-5.)

Hence, a peptide tag produced or developed from the protein may comprise a fragment of the protein of SEQ ID NO. 6 (or a sequence with at least 70, 80, 90 or 95% identity thereto) comprising the aspartic acid residue at position 101 and the binding partner produced from the protein may comprise a fragment of the protein of SEQ ID NO. 6 (or a sequence with at least 70, 80, 90 or 95% identity thereto) comprising the lysine residue at position 15. As discussed previously, particularly the peptide tag and binding partner may not both comprise the lysine at position 15 and the aspartic acid at position 101. Hence, if the peptide tag comprises the aspartic acid residue at position 101, it will not comprise the lysine at position 15 and if the binding partner comprises the lysine at position 15, it will not comprise the aspartic acid at position 101.

Therefore a peptide tag selected from CnaB2 may comprise a fragment of the amino acid sequence set out in SEQ ID NO. 6 including the reactive aspartic acid residue at position 101 and a binding partner may comprise a fragment of the amino acid sequence set out in SEQ ID NO. 6 including the reactive lysine residue at position 15.

Further, isopeptide bonds are known to spontaneously form between the subunits in the bacteriophage HK97 capsid. The bacteriophage HK97 capsid contains 420 subunits, where the final capsid maturation step creates 420 isopeptide bonds between proteins. In this example, each subunit is joined to its neighbour by the ligation of the side chain lysine at position 169 to asparagine at position 356. However, as discussed previously, since this is an example of intermolecular isopeptide bonding, the HK97 capsid subunits are not isopeptide proteins which can be used in the present invention. Thus, HK97 capsid subunits are excluded from being used to develop a peptide tag and binding partner pair as discussed herein.

Thus, any of these known proteins which are capable of spontaneously forming one or more isopeptide bonds intramolecularly may be used in the present invention to develop a peptide tag and binding partner pair which are able to spontaneously covalently bind via an isopeptide bond. Any of the isopeptide bonds in an isopeptide protein may be selected for the development of a peptide tag/binding partner pair. Preferably, the peptide tag and binding partner pair are chosen by carrying out the following method steps. Firstly, the residues in the isopeptide protein domain (a domain is an independently folding structural unit) which react to form an isopeptide bond may be selected (as discussed above, for Spy0128 N-terminal domain this is Lys 36 and Asn 168 and for Spy0128 C-terminal domain this is Lys 179 and Asn 303). The initial peptide selected from the isopeptide protein will comprise of one of the reactive residues for isopeptide formation along with a variable number of residues (typically at least 4) derived from the protein domain to the N-terminal or C-terminal side of this reactive residue, terminating on the N or C-terminal side before the next beta-sheet. Different length peptides may be expressed and their reaction rate with the binding partner may be tested by SDS-PAGE to define the optimal length of peptide. Further, the initial binding partner may consist of the protein domain lacking the reactive residue possessed by its peptide tag partner and furthermore lacking a variable number of residues derived from the beta-strand on which the peptide partner lies and from the loops surrounding the beta-strand on which the peptide tag partner lies. Different truncations of the binding partner may be expressed and their reaction rate with the peptide tested by SDS-PAGE, to define the optimal length of binding partner. The initial peptide tag and initial binding partner may then be subsequently modified by rational mutation (guided by the structure of the intact protein domain) or by library-based selection to enhance solubility, minimise non-specific reaction and increase reaction rate.

Further, homologues or mutants of the proteins which are capable of spontaneously forming one or more isopeptide bonds and which retain the ability to spontaneously form at least one isopeptide bond may be used in the invention. Thus, one or more of the residues of the proteins described above may be mutated e.g. substituted, deleted or inserted as compared to the wildtype (e.g. naturally occurring, known or published) sequence of the isopeptide protein. For example, 2, 3, 4, 5, 6, 7, 8, 9, 10 or more residues may be mutated compared to the wildtype (e.g. known or published) sequence of a protein capable of spontaneously forming an isopeptide bond. Such homologous or mutated proteins will be capable of producing a peptide tag and binding partner pair which are able to covalently bind according to the use of the present invention, as long as they can spontaneously form at least one isopeptide bond.

Preferably, a mutation made in close proximity to the reaction site (e.g. within 5, 10 or amino acids of the reaction site) in the isopeptide proteins discussed above may be a conservative amino acid substitution. Mutations made on the surface of protein partner may be quite different, e.g. to inactivate a binding surface to collagen previously possessed by the protein. Thus, although the substituted amino acid may be any one of the well known 20 conventional amino acids (Ala (A), Cys (C), Asp (D), Glu (E), Phe (F), Gly (G), His (H), Ile (I), Lys (K), Leu (L), Met (M), Asn (N), Pro (P), Gln (Q), Arg (R), Ser (S), Thr (T), Val (V), Trp (W) and Tyr (Y)), it is preferred that an amino acid substitution be made where an amino acid is replaced by another which preserves the physiochemical character of the polypeptide, particularly for a substitution which occurs in close proximity to the reaction site i.e. to either reactive residue (e.g. D may be replaced by E or vice versa, N by Q, or L; I by V or vice versa). Thus, generally the substituting amino acid has similar properties e.g. hydrophobicity, hydrophilicity, electronegativity, bulky side chains etc to the amino acid being replaced. Isomers of the native L-amino acid e.g. D-amino acids or amino acids not naturally present in the genetic code (including beta amino acids) may be incorporated. Alternatively, peptidomimetics may be incorporated into the sequence.

Additionally, it is preferred that the residues involved in the formation of one of the isopeptide bonds in the protein remain unchanged from those found in the wildtype protein sequence and/or be only substituted with other residues which are known to form isopeptide bonds. For example, if a mutation is made to a reactive asparagine, preferably this will consist of an amino acid substitution to aspartic acid or glutamine. Further, it is preferred that the glutamic acid residue which induces the formation of one isopeptide bond remain unmutated from the wildtype protein sequence or only be substituted with aspartic acid. Particularly, it is preferred that no mutation is made to a reactive lysine residue.

The formation of only one of the isopeptide bonds in an isopeptide protein is required to be preserved for that isopeptide protein to be used in the present invention. Thus, if an isopeptide protein comprises two isopeptide bonds for example, it is possible that mutations may be made which affect the ability of the protein to form one of the bonds, as long as the other bond is able to form.

A homologous protein which can be used in the present invention for the development or production of a peptide tag/binding partner pair may be at least 70% identical to the wildtype protein sequences set out above e.g. to the sequence of SEQ ID NO. 1, 3, 5 or 6 and more particularly may be at least 75, 80, 85, 90, 95, 96, 97, 98 or 99% identical to the protein sequences set out above e.g. SEQ ID NO.1, 3, 5 or 6. Furthermore, as discussed previously, such protein homologues must be capable of spontaneously forming one or more isopeptide bonds.

Amino acid sequence identity (or similarity) may be determined using the BESTFIT program of the Genetics Computer Group (GCG) Version 10 Software package from the University of Wisconsin. The program uses the local homology algorithm of Smith and Waterman with the default values: Gap creation penalty=8, Gap extension penalty=2, Average match=2.912, Average mismatch=2.003. The PILEUP and BLAST algorithms can be used to calculate homology or line up sequences. Software for performing BLAST analyses is publicly available through the National Center for Biotechnology Information (http://www.ncbi.nlm.nih.gov/). Particularly, in the present invention, identity is compared over the whole amino acid sequence.

Mutagenesis may be carried out using any of the well known methods of the art, e.g. site directed mutagenesis of the encoding nucleic acid sequence.

Other proteins which are capable of spontaneously forming one or more isopeptide bonds for use in the present invention may be identified by comparing their structures with those of proteins which are known to spontaneously form one or more isopeptide bonds. Particularly, other proteins which may spontaneously form an isopeptide bond may be identified by comparing their crystal structures with those from known isopeptide proteins e.g. the major pilin protein Spy0128 and in particular comparing the Lys-Asn-Glu/Asp residues often involved in the formation of an isopeptide protein. Additionally, other isopeptide proteins may be identified by screening for structural homologues of known isopeptide proteins using the Protein Data Bank and the SPASM server (http://eds.bmc.uu.se/eds/span-a.php?spasm)

may be used to target the 3D structural template of Lys-Asn-Glu/Asp of the isopeptide bond.

Alternatively, proteins which form isopeptide bonds may be designed de novo for use in the present invention. As discussed above, such proteins should possess the two required reactive amino acid residues for the spontaneous formation of the isopeptide bonds, together with a glutamic acid or aspartic acid residue which would preferably be within 6.5 Angstrom to either or preferably both of the residues involved in the isopeptide bond e.g. within 6.0, 5.5, 5.0, 4.5, 4.0, 3.5 or 3.0 Angstrom. These distances particularly refer to the distances between the relevant atoms within each residue i.e. the atoms involved in forming the isopeptide bond. Particularly, the two residues (and more particularly, their relevant atoms) involved in the bond should be within 4 Angstrom from each other in space, preferably 3.8, 3.6, 3.4, 3.2, 3.0, 2.8, 2.6, 2.4, 2.2, 2.0, 1.8 or 1.6 Angstrom.

The pKa of residues should also be considered when designing an isopeptide protein de novo. Particularly, it is preferred that the reactive lysine residue be deprotonated before reaction, which at neutral pH may require the lysine to be buried in the hydrophobic core.

Rosetta can be used to design isopeptide proteins de novo and this software can be found at http://depts.washington.edu/ventures/UW Technology/Express Licenses/rosetta.php. (See also Macromolecular modeling with rosetta, Das. R, Baker. D, Annu Rev Biochem, 2008, 77, 363-82). Additionally, the RASMOT-3D PRO server can be used to search the protein database for appropriate orientation of residues at http://biodev.extra.cea.fr/rasmot3d/.

Thus, as discussed above, once an isopeptide protein has been identified, produced, or de novo designed which is capable of spontaneously forming an isopeptide bond, this may be used in the present invention to develop/produce a peptide tag and binding partner pair which will reconstitute by covalently bonding to each other.

The term "peptide tag" as used herein generally refers to a small peptide fragment which may or may not be designed or derived directly from the isopeptide protein. Thus, although the peptide tag can be based upon a sequence of a fragment of an isopeptide protein, it is possible that the sequence of the peptide tag may vary from the sequence of the isopeptide protein or a fragment thereof which is used to design the binding partner. Particularly, the binding partner derived from an isopeptide protein may be used to screen a peptide library to identify a peptide tag which binds thereto with greater efficiency than a peptide tag based entirely on the sequence of a fragment of the isopeptide protein. Thus the peptide tag may or may not be homologous to a fragment of the isopeptide protein.

In this respect, a peptide tag may be between 5-50 amino acids in length e.g. from 10, 20, 30, 40 to 50 amino acids in length and may bind covalently via an isopeptide bond to a binding partner as defined below which is derived from an isopeptide protein. Thus, the peptide tag may comprise one reactive residue involved in an isopeptide bond in the isopeptide protein used to design the binding partner (and the binding partner may comprise the other reactive residue involved in that bond). Hence, the peptide tag preferably may be 5-50 amino acids in length, binds covalently via an isopeptide bond to a binding partner as defined below (which is derived from an isopeptide protein and which comprises one reactive residue from an isopeptide bond of the isopeptide protein) and comprises the other reactive residue from the isopeptide bond in the isopeptide protein used to design the binding partner. If the peptide tag is fused to another polypeptide or protein, then the length of the fusion protein (i.e. the peptide tag and protein) may be greater than 50 amino acids in length. However, the peptide tag portion of the fusion will typically be 5-50 amino acids, as discussed above.

A peptide tag therefore does not consist of the entire protein sequence of an isopeptide protein and is shorter in length. Thus, a peptide tag may comprise less than 5, 10, 20, 30, 40 or 50% of the number of amino acid residues present in the isopeptide protein and may comprise mutations or alterations as compared to the isopeptide protein's corresponding sequence.

If a peptide tag is directly designed using an isopeptide protein then, the peptide tag may (i) comprise or consist of a fragment of an isopeptide protein wherein the fragment is at least 5 amino acids in length or a sequence with at least 50% identity to the fragment e.g. with at least 55, 60, 65, 70, 75, 80, 85, 90, 95, 96, 97, 98 or 99% identity, and (ii) is less than 50 amino acids in length.

The peptide tag may comprise or consist of a fragment of the isopeptide protein which is at least 5 amino acids in length e.g. at least 6, 7, 8, 9, 10, 11, 12, 13, 14, 15, 16, 17, 18 or 19 amino acids in length.

As discussed above, the peptide tag may consist of less than 50 amino acid residues, for example less than 50, 40, 30, 20 or 10 amino acid residues. Particularly, the peptide tag may consist of 3, 4, 5, 6, 7, 8, 9, 10, 11, 12, 13, 14, 15, 16, 17, 18 or 19 amino acid residues. The small size of the peptide tag may allow its use in labelling proteins of interest and/or may prevent the peptide tag from interfering with the function or activity of the protein of interest. Thus, proteins of interest which are labelled with small peptide tags may have the same structure, folding and function as proteins of interest which are unlabelled. As discussed above, the fusions between the peptide tag and another protein or polypeptide may be greater in length than 50 amino acids but the peptide tag portion is as defined previously.

As previously discussed, the peptide tag should be able to covalently bind to a binding partner developed from the isopeptide protein via an isopeptide bond spontaneously. In this respect, the peptide tag preferably comprises one of the reactive amino acid residues involved in the formation of an isopeptide bond in the isopeptide protein. Hence, preferably the peptide tag does not comprise the other reactive residue involved in the formation of the isopeptide bond. The peptide tag comprises only one reactive residue from the isopeptide bond and does not comprise both reactive residues involved. Further, if the peptide tag comprises a fragment of the isopeptide protein which is modified or mutated, it is preferred that the reactive residue in that fragment remains unchanged. Thus, a peptide tag may (i) comprise or consist of a fragment of an isopeptide protein wherein the fragment is at least 5 amino acids in length or a sequence with at least 50% identity to the fragment e.g. with at least 55, 60, 65, 70, 75, 80, 85, 90, 95, 96, 97, 98 or 99% identity, (ii) is less than 50 amino acids in length and (iii) comprises one reactive residue involved in the isopeptide bond in the isopeptide protein.

The term "binding partner" as used herein, refers generally to a protein or peptide which is derived or designed from the isopeptide protein and which may covalently bind to a peptide tag which as discussed above is a small peptide fragment usually designed or derived from the same isopeptide protein. Thus, the binding partner may not be size limited and may comprise or consist of any amount of the isopeptide protein but typically does not comprise the reactive residue involved in the isopeptide bond which is found in the peptide tag. Therefore, the binding partner typically comprises a fragment of the isopeptide protein and does not comprise the whole isopeptide protein (at least the reactive residue found in the corresponding peptide tag should be excluded). Generally, the binding partner is larger than its corresponding peptide tag and comprises or consists of a larger fragment or portion of the isopeptide protein compared to the peptide tag. The binding partner may comprise a fragment of the isopeptide protein which overlaps with a fragment designed to constitute a peptide tag or may comprise a discrete and separate fragment of the isopeptide protein compared to that of the peptide tag. Thus, the sequence of the binding partner may overlap with that of the designed peptide tag or the peptide tag and binding partner may comprise or consist of two discrete fragments of the isopeptide protein (or as discussed above, the peptide tag may not be based on the sequence of the isopeptide protein).

Particularly, the binding partner refers to a peptide/protein which comprises or consists of a fragment of an isopeptide protein which is at least 20 amino acids in length, or a sequence which is at least 70% identical thereto, for example 75, 80, 85, 90, 95, 96, 97, 98 or 99% identical. Preferably, the fragment may be at least 50, 60, 70, 80, 90, 100, 125, 150, 175, 200, 225, 250, 275, 300, 325 or 350 amino acids in length. As discussed above, the binding partner is not size limited (although preferably excludes any peptide tag sequence which is derived from the same isopeptide protein or excludes the reactive residue which is included in the peptide tag), but should covalently bind to a peptide tag developed from the isopeptide protein. In this respect, the binding partner preferably comprises one of the reactive residues involved in the formation of an isopeptide bond in the isopeptide protein.

Thus, "a peptide tag and binding partner pair" as discussed herein refers to a binding partner (a peptide/protein) developed using an isopeptide bond in an isopeptide protein and a peptide tag which binds thereto via an isopeptide bond. As discussed above, the sequence of the peptide tag may vary from the isopeptide protein sequence (or a fragment thereof) which is used to design the binding partner. A peptide tag and binding partner pair will covalently bind to one another via an isopeptide bond and thus preferably the peptide tag comprises one of the reactive residues involved in one isopeptide bond in the isopeptide protein used to design the binding partner and the binding partner comprises the other reactive residue involved in that isopeptide bond in the isopeptide protein.

At least the binding partner may therefore be designed and/or produced based on the sequence of an isopeptide protein. The peptide tag may also be designed using the same isopeptide protein sequence and isopeptide bond as the binding partner or may be obtained for example by screening a peptide library using the binding partner. It may also be possible to select an alternative binding partner by screening protein libraries. For example, phage display libraries of short peptides or proteins may be screened to determine whether any covalent interactions occur between any of the peptide tags or the binding partners of the invention and to select for peptide tags or binding partners where reaction is faster in a particular condition (e.g. acidic conditions or at 4° C. or in the presence of denaturant). Phage display libraries are commonly used to select for non-covalent binding partners, with moderate to high affinity interactions remaining bound with washes at neutral pH and sometimes high salt or detergent, but typically breaking upon incubation with glycine-HCl pH 2.2 (e.g. An improved selection procedure for the screening of phage display peptide libraries, J Immunol Methods, 2001, 247(1-2), 191-203). To favour selection of covalent interactions over-non-covalent interactions, high affinity non-covalent interactions to the phage can be broken under harsher conditions, including temperature greater than 37° C., buffer containing more than 1M guanidinium hydrochloride and washes prolonged for hours to days—conditions under which phage remain infectious (Jung et al, J. Mol. Biol., 1999, 294(1), 163-80). Peptide tags or binding partners isolated by phage display may be recombinantly expressed in E. coli, purified and tested e.g. by mass spectrometry to confirm their ability to form a covalent bond upon reaction with the cognate peptide tag or binding partner.

Hence, by examining the positioning of the (reactive) residues involved in the formation of the isopeptide bond in the isopeptide protein, it is possible to design a peptide tag and binding partner pair which will covalently bind to each other (e.g. spontaneously via an isopeptide bond). As discussed previously, the peptide tag comprises one of the reactive residues involved in the isopeptide bond in the isopeptide protein and the binding partner comprises the other reactive residue involved in the isopeptide bond in the isopeptide protein. Thus, the peptide tag and binding partner pair from the isopeptide protein are designed using this main criterion. Further, as previously discussed, a glutamic acid or aspartic acid residue which may be required to direct the formation of an isopeptide bond may be present in either the peptide tag or binding partner.

Thus, as indicated previously, in order to produce a peptide tag and binding partner pair, residues in the isopeptide protein domain which react to form an isopeptide bond may be identified. The initial peptide selected from the isopeptide protein will comprise of one of the reactive residues for isopeptide formation along with a variable number of residues (typically at least 4) derived from the protein domain to the N-terminal or C-terminal side of this reactive residue, terminating on the N or C-terminal side before the next beta-sheet. Different length peptides may be expressed and their reaction rate with the binding partner may be tested by SDS-PAGE to define the optimal length of peptide. Further, the initial binding partner may consist of the protein domain lacking the reactive residue possessed by its peptide tag partner and furthermore lacking a variable number of residues derived from the beta-strand on which the peptide partner lies and from the loops surrounding the beta-strand on which the peptide tag partner lies. Different truncations of the binding partner may be expressed and their reaction rate with the peptide tested by SDS-PAGE, to define the optimal length of binding partner. The initial peptide tag and initial binding partner may then be subsequently modified by rational mutation (guided by the structure of the intact protein domain) or by library-based selection to enhance solubility, minimise non-specific reaction and increase reaction rate.

Further, when designing a peptide tag and binding partner from an isopeptide protein, it is preferable that the reactive residues be exposed in the peptide tag and/or binding partner for interaction with each other. However, particularly for the binding partner, the reactive residue may be only occasionally exposed, for example since the protein may close up to compensate for the loss of the peptide tag portion from the protein (e.g. which may constitute a n-strand). For the corresponding peptide tag, the reactive residue generally however is exposed.

When designing a peptide tag and binding partner from an isopeptide protein comprising more than one isopeptide bond, it is preferable that the isopeptide bond involving a residue nearest to the N or C terminal ends of the isopeptide protein is firstly considered. In this respect, the terminal part of the sequence may be easily used to design or produce the relatively short peptide tag (comprising one of the reactive residues involved in the isopeptide bond) as discussed above, and the remainder of the isopeptide protein (or a portion or a fragment thereof which may or may not overlap with the peptide tag sequence) can be used to form the binding partner for the peptide tag.

The peptide tag and binding partner pair of the present invention may therefore be designed from an isopeptide protein and as discussed in detail further below may then be produced. Production may use chemical synthesis methods well known in the art or can involve the use of recombinant DNA technology, e.g. where the peptide tag is co-expressed from the same vector as a protein of interest. Further, the peptide tag and binding partner of the invention may be produced directly from the encoding sequence of an isopeptide protein by cleaving the coding sequence of the protein at the required site to form the two fragments. I Thus, the term "development" as used herein refers to the design and production of a peptide tag and binding partner pair. As discussed in detail above, at least the binding partner is designed using an isopeptide protein i.e. based on the sequence of such a protein and the position of an isopeptide bond therein. The peptide tag may also be designed based on the same isopeptide protein sequence or may be identified by screening a peptide library with the binding partner. Once the binding partner has been designed using the isopeptide protein and the peptide tag which binds thereto has been designed or identified, they may be produced. As indicated above, production of the peptide tag and binding partner may be by various methods known in the art, but particularly, the production of these entities need not involve the isopeptide protein which was used for their design. Thus, the production is an independent step which may or may not involve the isopeptide protein. "Development" hence refers to the design of the binding partner using the isopeptide protein, the design or identification of the peptide tag (e.g. by using the same isopeptide protein and isopeptide bond as for the binding partner or by screening a peptide library using the binding partner) and to the subsequent production of the peptide tag and binding partner using any known method. The term "production" which refers to the final result i.e. the production of the peptide tag and binding partner may also be used interchangeably with the term "development".

Hence, alternatively viewed, the present invention provides a method of developing or producing a peptide tag and binding partner pair which are capable of spontaneously binding to each other by forming an isopeptide bond comprising the steps of (a) selecting an isopeptide protein, (b) identifying the position of an isopeptide bond in said protein, (c) designing a binding partner from said protein wherein said binding partner comprises one reactive residue involved in the isopeptide bond, (d) either designing a peptide tag from said protein or screening a peptide library using the binding partner to identify a peptide tag wherein said peptide tag comprises the other reactive residue involved in the isopeptide bond and (e) producing the peptide tag and binding partner pair. As discussed previously, preferably the binding partner will not comprise the other reactive residue involved in the isopeptide bond i.e. the binding partner only comprises one reactive residue.

If both the peptide tag and binding partner in the above method are designed using the isopeptide protein sequence, then the method may also comprise an additional step wherein a peptide library is screened using the binding partner to identify a further peptide tag e.g. a peptide tag with improved properties. Screening may be with chemically synthesised peptide libraries or with genetically expressed peptide libraries, such as from bacterial display, phage display, ribosome display, mRNA display, yeast display or comparable genetic screening methods. The screening of a phage library is discussed previously.

The peptide tag and/or binding partner may be fused to other proteins or polypeptides, at the N- or C-terminus of such proteins or polypeptides or in an internal loop. Particularly, a spacer may flank the peptide tag or binding partner e.g. a glycine/serine rich spacer, in order to enhance accessibility for reaction. The spacer may include a site for specific proteolysis (e.g. by Factor X, thrombin, enterokinase or tobacco etch virus NIa protease), allowing specific release from solid phase capture.

Further, the peptide tag and binding partner may be separately fused to proteins in the same living cell or in different cells of the same living organism in order to artificially bring proteins or cells together. In another embodiment, the peptide tag and binding partner may be placed at different ends of the same protein (i.e. not adjacent to one another), so that reaction to form an isopeptide bond could lead to either protein multimerisation or circularisation of the protein.

The isopeptide bond is preferably a chemical bond or a covalent bond which forms between the peptide tag and binding partner described herein which is stable after heating at 95° C. for 7 minutes in a solution containing at least 1% sodium dodecyl sulfate (SDS). Such a bond is generally considered to be irreversible. The covalent bonding of the peptide tag and binding partner may occur under any conditions e.g. from −20° C. to 100° C. and from pH 2-10, but particularly may occur at a temperature range from 4-37° C. and at a pH range from 5-8.

Thus, an isopeptide protein can be used to develop or produce a peptide tag and binding partner pair. In this respect, the invention also encompasses a peptide tag and binding partner pair wherein a) said peptide tag (i) is from 5 to 50 amino acids in length and (ii) comprises one reactive residue involved in an isopeptide bond in an isopeptide protein;

b) said binding partner (i) comprises a fragment of said isopeptide protein which is at least 20 amino acids in length or a sequence which has at least 70% identity thereto and (ii) comprises the other reactive residue involved in the isopeptide bond in said isopeptide protein and c) said peptide tag and binding partner are capable of binding to each other via an isopeptide bond. The binding partner does not include or comprise the full length isopeptide protein and only comprises one of the reactive residues involved in the isopeptide bond of interest. Therefore the binding partner does not comprise the reactive residue present in the peptide tag.

In a preferred embodiment, the isopeptide protein which is the major pilin protein Spy0128 from *Streptococcus pyogenes* is used in the invention to develop/produce a peptide tag and binding partner pair which are capable of covalently binding to each other. As discussed previously, this protein comprises two isopeptide bonds which may each be used to design/produce a peptide tag and binding partner according to the present invention. One of the isopeptide bonds occurs in the final β strand of the C-terminal domain and the other isopeptide bond occurs in the first β strand of the N-terminal domain of the protein.

Hence, the invention provides a peptide tag and binding partner pair as described above wherein said peptide tag and/or binding partner pair are obtainable from the major pilin protein of *Streptococcus pyogenes*.

In this respect, a C-terminal fragment of major pilin protein Spy0128, which comprises one of the reactive residues involved in the isopeptide bond in the final β strand of the C-terminal domain, may constitute a peptide tag and the remaining, truncated or overlapping fragment of the major pilin protein may form a binding partner for the C-terminal peptide tag. In a preferred embodiment, the major pilin protein Spy0128 may be used to design a C-terminal fragment peptide tag as discussed above which comprises the asparagine residue involved in the isopeptide bond in the final β strand of the C-terminal domain. Further, the binding partner may comprise the lysine residue involved in the isopeptide bond in the final β strand of the C-terminal domain in the isopeptide protein.

Particularly, the invention provides a peptide tag comprising residues 302-308 of the sequence set out in SEQ ID NO. 1 or a sequence with at least 70% identity thereto wherein said peptide tag is less than 50 amino acids in length. More particularly, the peptide tag designed from the major pilin protein Spy0128 may comprise residues 301-308, 300-308, 299-308, 298-308, 297-308, 296-308, 295-308, 294-308, 293-308, 292-308, 291-308 or 290-308 of SEQ ID NO. 1 or a sequence with at least 70% identity thereto. Preferably the peptide tag comprises the reactive asparagine of position 303 i.e. this residue is preferably unchanged. Further, the peptide tag may be a fragment of SEQ ID NO. 1. In a preferred embodiment, the invention provides a peptide tag which comprises residues 293-308 of the sequence set forth in SEQ ID NO. 1 or which comprises a sequence with at least 70% identity thereto. The peptide tags are length restricted and comprise less than 50 amino acid residues. Thus the peptide tags do not comprise the sequence of SEQ ID NO. 1 but only specific fragments thereof, or sequences with at least 70% identity e.g. 75, 80, 85, 90 or 95% identity to such specific fragments.

Preferably, the corresponding binding partner, for the above described peptide tag, comprises or consists of residues 31-291 of the sequence set out in SEQ ID NO. 1, or a sequence with at least 70% identity thereto e.g. with 75, 80, 85, 90, 95, 96, 97, 98 or 99% identity, excluding the sequence set out in SEQ ID NO. 1. Thus, this binding partner comprises the reactive lysine residue involved in the isopeptide bond in the final β strand of the C-terminal domain in the isopeptide protein. Hence, preferably the reactive lysine residue from position 179 of SEQ ID NO. 1 should be present in the binding partner and should not be mutated. Particularly, the binding partner comprises residues 31-292, 31-293, 31-294, 31-295, 31-296, 31-297, 31-298, 31-299, 31-300, 31-301 or 31-302 of the sequence set forth in SEQ ID NO. 1 or a sequence with at least 70% identity thereto, excluding the sequence of SEQ ID NO. 1. Preferably, the binding partner is a fragment of SEQ ID NO. 1.

Thus particularly, any one of the above binding partners may covalently bind to a peptide tag obtainable from the major pilin protein Spy0128 which comprises residues 302-308 of the sequence set out in SEQ ID NO. 1 or a sequence with at least 70% identity thereto. Hence, the reactive asparagine in the peptide tag will be able to form an isopeptide bond with the reactive lysine residue comprised in the binding partner and the resultant bonding will be irreversible.

Thus, the invention further provides a peptide tag and binding partner pair wherein said peptide tag comprises residues 302-308 of the sequence set out in SEQ ID NO. 1 or a sequence with at least 70% identity thereto and is less than 50 amino acids in length and said binding partner comprises residues 31-291 of the sequence set out in SEQ ID NO. 1 or a sequence with at least 70% identity thereto wherein said peptide tag and said binding partner are capable of covalently binding to each other via an isopeptide bond. Preferably as stated above the peptide tag comprises the reactive asparagine of position 303 and the binding partner comprises the reactive lysine of position 179.

Additionally, a peptide tag may be designed from the major pilin protein Spy0128 using the alternative isopeptide bond in the N-terminus. Therefore, a peptide tag may be designed or is obtainable from an N-terminal fragment of the isopeptide protein and the remaining, truncated or overlapping protein fragment may constitute the binding partner.

The reactive lysine involved in the isopeptide bond at the N-terminus is found at position 36 of SEQ ID NO. 1 and the reactive asparagine involved in the isopeptide bond is found at position 168 of SEQ ID NO.1. (The glutamic acid which induces isopeptide bond formation is present at residue position 117 of SEQ ID NO. 1). Thus, in a preferred embodiment the peptide tag may comprise the reactive lysine residue in this instance and the binding partner may comprise the reactive asparagine.

Particularly, the invention provides a peptide tag which comprises residues 31-40 of the sequence set out in SEQ ID NO. 1 or a sequence with at least 70% identity thereto and is less than 50 amino acids in length. Particularly, the peptide tag may be a fragment of SEQ ID NO. 1 which comprises residues 31-40 of the sequence set out in SEQ ID NO. 1.

The corresponding binding partner for the above described peptide tag comprises residues 37-304 of the sequence set out in SEQ ID NO. 1 or has a sequence with at least 70% identity thereto, excluding the sequence of SEQ ID NO. 1. Preferably, the reactive residues in the peptide tag and binding partner are not mutated.

The peptide tags and binding partners of the invention do not include sequences of SEQ ID NO. 1.

In a further preferred embodiment of the invention, the isopeptide protein of ACE19 from *E. faecalis* (SEQ ID NO. 3) is used in the invention to develop a peptide tag and binding partner pair which are capable of covalently binding to each other.

In this respect, the invention provides a peptide tag and binding partner pair as described above wherein said peptide tag and binding partner are obtainable from ACE19 of *E. faecalis*.

Thus, particularly, the invention provides a peptide tag which comprises residues 179-184 e.g. 173-185 of the sequence set out in SEQ ID NO. 3 or has a sequence with at least 70% identity thereto and is less than 50 amino acids in length. Particularly, the peptide tag may be a fragment of SEQ ID NO. 3.

The corresponding binding partner for the above peptide tag, which is also provided by the present invention comprises residues 191-317 e.g. 186-318 of SEQ ID NO. 3 or a sequence having at least 70% identity thereto, excluding SEQ ID NO. 3.

Neither the peptide tag nor the binding partner consist or comprise SEQ ID NO. 3.

Further, a peptide tag and binding partner pair are encompassed wherein said peptide tag comprises residues 179-184 e.g. 173-185 of the sequence set out in SEQ ID NO. 3 or has a sequence with at least 70% identity thereto and is less than 50 amino acids in length and said binding partner comprises residues 191-317 e.g. 186-318 of SEQ ID NO. 3 or a sequence having at least 70% identity thereto wherein said peptide tag and binding partner are capable of covalently binding to each other via an isopeptide bond. Preferably the reactive residues in the peptide tag and binding partner are not mutated.

In another preferred embodiment of the invention, the CnaB2 domain of the isopeptide protein of FbaB from *Streptococcus pyogenes* (SEQ ID NO. 6) is used in the invention to develop a peptide tag and binding partner pair which are capable of covalently binding to each other. Neither the peptide tag nor the binding partner comprise SEQ ID NO. 6. Thus, preferably, the peptide tag and binding partner are fragments of SEQ ID NO. 6, or comprise a fragment of SEQ ID NO. 6 or a sequence with at least 70, 80, 90 or 95% identity thereto. Preferably, the peptide tag comprises the reactive aspartic acid residue of position 101 of SEQ ID NO. 6 and the binding partner comprises the reactive lysine of position 15 of SEQ ID NO. 6.

As discussed above however, all of the binding partners described herein may be used to screen a peptide library to identify a further peptide tag(s) which covalently binds thereto. Thus, the binding partners described herein may be used with other peptide tags which are 5-50 amino acids in length and comprise the other reactive residue present in the isopeptide bond from which the binding partner is developed (the binding partner comprises one reactive residue from the isopeptide bond in the isopeptide protein and the peptide tag comprises the other reactive residue).

Mutations or alterations may be made to any of the peptide tags and/or binding partners of the present invention which are obtainable from an isopeptide protein e.g. which are fragments of an isopeptide protein, as long as the resulting peptide tags and their respective binding partners are capable of covalently bonding. Thus, as discussed above, one or more residues in the peptide tag or binding partner may be substituted or deleted and/or one or more residues may be inserted compared to the sequences of the peptide tags and/or binding partners obtained/designed from an isopeptide protein. Mutations which may be made are discussed above in terms of the isopeptide protein, and these comments apply here also.

Thus, as described above, the peptide tags and/or binding partners of the invention include fragments of an isopeptide protein sequence or sequences which are at least 70% identical thereto. Thus, such sequences with at least 70% identity may comprise one or more mutations or alterations compared to the peptide tag and binding partners which are fragments or are obtainable from the isopeptide proteins.

It may be desirable particularly to introduce mutations or alterations which may improve the properties of either or both of the peptide tag and/or binding partner. Thus, for example, it may be possible to improve the solubility of the peptides by making a mutation. For the peptide tag designed from the C-terminal domain of the final β sheet of major pilin protein Spy0128, it may be possible for example to improve the solubility by substituting residue 307 (phenylalanine in SEQ ID NO. 1) with a less hydrophobic amino acid such as alanine. Thus, the peptide tags and binding partners discussed above may be mutated and such mutants are encompassed by the present invention.

Preferably, as discussed above, the invention provides a peptide tag comprising residues 302-308 of SEQ ID NO. 1 or comprising residues 31-40 of SEQ ID NO. 1 or a peptide tag which has at least 70% identity thereto wherein the peptide tag is less than 50 amino acids in length. Alternatively viewed, such peptide tags may comprise one amino acid substitution in the amino acid sequence corresponding to amino acids residues 302-308 or 31-40 of SEQ ID NO. 1. However, as discussed previously, such peptide tags must retain their ability to covalently bond to their corresponding binding partners.

Mutations or alterations may also be made to the binding partners compared to the sequence of the isopeptide protein used to design or produce the binding partners (and peptide tags). Thus, as discussed above, a binding partner comprising residues 31-291 or comprising residues 37-304 of SEQ ID NO. 1 or a binding partner which has at least 70% identity thereto, excluding SEQ ID NO. 1 is encompassed by the present invention. Particularly, the binding partner may be a fragment of SEQ ID NO. 1.

It may also be possible to use a binding partner of the invention to screen for improved peptide tags. Thus, as discussed above, it is possible that the peptide tag sequence which is a fragment of the isopeptide protein is not optimal and that mutated or altered peptide tags may be developed which would for example bind to the binding partner more rapidly. In order to identify such improved peptide tags, it may be possible to screen peptide libraries using a binding partner of the invention. For example, phage display libraries of short peptides may be screened to determine whether any covalent interactions occur between any of the peptides and the binding partners of the invention. As discussed previously, covalent interactions may be selected by applying harsh conditions such as temperatures greater than 37° C., buffer containing more than 1M guanidinium hydrochloride and prolonged washes e.g. for hours to days. Any peptides which covalently bind to the binding partner of the invention may be investigated by recombinant expression to determine the speed and stability of the bond formation. Thus, the invention provides a use of a binding partner of the invention for identifying a peptide which will covalently bind thereto. Additionally, it is possible to identify a binding partner for a peptide tag by screening a protein library. The peptide tag of the invention can be used to identify a binding partner which will covalently bind thereto.

The peptide tags and/or binding partners of the invention may be fused or conjugated to other molecules or to other entities e.g. to a nucleic acid molecule, protein, peptide, small-molecule organic compound, metal-ligand complex, polysaccharide, nanoparticle, nanotube, polymer or any combination of these. As discussed previously, such fusions may be any length, although the peptide tag portion of the fusion may not be greater than 50 amino acids. In particular, the peptide tag and/or binding partner may be conjugated to a compound which has a therapeutic or prophylactic effect e.g. an antibiotic, antiviral, vaccine, antitumour agent e.g. a radioactive compound or isotope, cytokines, toxins, oligonucleotides and nucleic acids encoding genes or nucleic acid vaccines. The peptide tag and/or binding partner may further be conjugated to a label, for example a radiolabel, a fluorescent label, luminescent label, a chromophore label as well as to substances and enzymes which generate a detectable substrate e.g. horse radish peroxidase, luciferase or alkaline phosphatase. This detection may be applied in numerous assays where antibodies are conventionally used, including Western blotting/immunoblotting, histochemistry, enzyme-linked immunosorbent assay (ELISA), or flow cytometry (FACS) formats. Labels for magnetic resonance imaging, positron emission tomography probes and boron 10 for neutron capture therapy may also be conjugated to the peptide tag and/or binding partner of the invention. Particularly, the peptide tag and/or binding partner may be fused or produced with another peptide, for example His6 tag, and/or may be fused or produced with another protein, for example with the purpose of enhancing recombinant protein expression by fusing to Maltose Binding Protein.

A further aspect of the present invention concerns a nucleic acid molecule which comprises a nucleotide sequence encoding a peptide tag or encoding a binding partner of the invention. The nucleic acid molecule may further comprise a nucleotide sequence or gene encoding a protein of interest, wherein the gene encoding the protein of interest and the peptide tag or binding partner may be co-transcribed and expressed and may hence be operably linked.

Additionally, a vector comprising a nucleic acid molecule of the invention is also provided. Typically, the nucleic acid molecule may be operably linked to a control sequence present in the vector e.g. a promoter which is capable of providing for the expression of the coding sequence in a host cell. Thus, in addition to the nucleic acid sequence of the invention, the vectors may comprise other elements such as a promoter, enhancer, transcription initiation site, termination site, translation initiation site etc. Further, the vector may comprise one or more selectable marker genes such as a gene providing ampicillin resistance or kanamycin resistance. The vector may additionally comprise a signal sequence, allowing export of an expressed product outside of the host cell or to a particular cellular compartment or organelle.

The vector is generally selected depending on the intended expression system and may be a transposon, artificial chromosome, plasmid, virus or phage vector. The vector may be typically introduced into host cells using conventional techniques such as calcium phosphate precipitation, liposomal transfection agents, DEAE-dextran transfection, viral transduction, microinjection or electroporation.

A further aspect of the present invention concerns a cell which is transformed or transfected with a vector or nucleic acid molecule of the invention. Thus, the cell may carry at least one copy of a nucleic acid sequence of the invention and the cell may be a prokaryotic cell such as *E. coli* or a eukaryotic cell such as a yeast. Further, non-human transgenic organisms are encompassed which are transformed or transfected with a vector or nucleic acid sequence of the invention. Such vectors or nucleic acids may be stably inserted to allow the production of progeny comprising the transgene. Thus, the non-human transgenic organism of the invention comprises at least one copy of the nucleic acid sequence of the invention e.g. within its genome. Examples of non-human transgenic organisms include archaea, bacteria, fungi, plants, mice, rats, rabbits, sheep, cows etc. and also transgenic viruses used for research or therapeutic purposes.

In another aspect of the invention, a process for the production of the peptide tag or binding partner of the invention is provided which comprises the following steps:
  a) transforming or transfecting a suitable host cell with a vector which comprises a nucleotide sequence encoding the peptide tag or binding partner of the invention,
  b) culturing the host cell under conditions which allow expression of the peptide tag or binding partner, and
  c) isolating the peptide tag or binding partner.

The process may further include steps of selecting the peptide tag and binding partner from an isopeptide protein as discussed above.

As discussed above, the peptide tag or binding partner may be produced attached or linked to another entity e.g. to another peptide or protein, and the recombinant process described above would be suitable for producing such molecules.

Therefore, the peptide tag and binding partner may be produced using recombinant methodology. It will be understood that the production process may comprise additional steps such as a step of producing the vector which comprises a nucleotide sequence encoding the peptide tag or binding partner. Alternatively, the peptide tag or binding partner may be produced by chemical synthesis (e.g. by solid phase synthesis of peptides in which the C-terminal amino acid of the sequence is attached to an insoluble support followed by sequential addition of the remaining amino acids).

The present invention also provides a kit comprising a peptide tag and a binding partner pair of the invention. The peptide tag and/or binding partner in the kit may be attached or conjugated to another entity as discussed previously. Thus, particularly, the peptide tag may be linked to another peptide or protein and/or the binding partner may be attached to a solid support or vice versa. A solid support includes a solid surface such as a plate (including a protein chip), column, nanoparticle or microsphere.

Preferably, however, the kit may comprise a vector encoding a peptide tag and/or either a vector encoding a binding partner or a binding partner wherein said peptide tag and binding partner are obtainable from a protein which is capable of spontaneously forming at least one isopeptide bond and wherein said peptide tag and binding partner will covalently bind to each other.

In this embodiment, the vector encoding a peptide tag may further encode a protein of interest, wherein the peptide tag and protein of interest may be expressed as a single linked protein.

Particularly, the kit of the invention may comprise the peptide tags and binding partners or the vectors encoding the peptide tags and binding partners of the invention or a combination thereof.

Additionally, the kits of the invention which comprise one or more vector constructs may further comprise cells to allow the expression of the peptide tag and/or binding partner. Alternatively, the kit may comprise transformed or transfected host cells.

The peptide tag and binding partner pairs of the invention or the kit of the invention comprising the peptide tag and binding partner may be used for any purpose for which a label and its binding partner may be used in the art. However, as discussed above, the peptide tag and binding partner designed according to the present invention may be particularly useful in methods when peptide attachment must be stable over long periods, e.g. in imaging methods, or when proteins are subject to high forces, such as shear in the blood-stream or from the firing of molecular motors.

The binding partner and peptide tag may be used in preparative methods where for example the binding partner may be immobilised to a solid support and used to capture peptide tagged entities e.g. molecules, nanoparticles, cells etc which are passed over the solid support. The peptide tagged entities will be captured by the binding partner and may then be detected e.g. by application of a labelled antibody, or proteolysis followed by mass spectrometry, or by sequencing of co-purified nucleic acids (DNA or RNA). In this way, it may be possible to purify a peptide tagged entity from a composition/solution comprising other entities by virtue of its binding to the binding partner designed according to the invention.

Thus, the invention provides a method of capturing an entity e.g. a molecule (protein, DNA etc.) labelled with a peptide tag of the invention comprising the step of passing the peptide tagged entity over an immobilised binding partner of the invention for that peptide tag.

Further, the invention provides a method of purifying an entity labelled with a peptide tag of the invention from a sample comprising the step of passing the peptide tagged entity over an immobilised binding partner of the invention which covalently binds the peptide tag. This may be applied in immunoprecipitation to isolate specific proteins from complex mixtures, e.g. cell lysates, or in co-immunoprecipitation to isolate the interacting partners of proteins from complex mixtures, including where such partners are DNA (chromatin immunoprecipitation, ChIP) or RNA, where this nucleic acid may be subsequently analysed by hybridisation or sequencing. Alternatively the binding partner may be linked to magnetic beads, allowing magnetic purification of the peptide tag linked to a protein, protein-complex or cell from an impure mixture. The covalent nature of the peptide-binding partner interaction described here should impart higher resistance to force than a non-covalent peptide-protein interaction and so should survive harsher washing, which should enable higher purity isolation.

Additionally, the peptide tags and binding partners of the invention may be used in diagnostic methods to bind and detect entities. In such diagnostic methods, typically, the presence of an entity in a sample obtained from a patient may indicate the presence or absence of a condition. For example, some disease conditions may result in the expression of a particular protein which is not usually produced (or is produced in a different amount) in a subject without the condition and this protein can therefore act as a marker for the condition. In order to detect any such markers in a sample obtained from a patient, antibodies labelled with a peptide tag of the invention directed to the marker may be added so that any markers in the sample are peptide tagged with the peptide tag of the invention. Such peptide tagged proteins may then be captured by a binding partner of the invention which is able to covalently bind to the peptide tag and thereby achieve detection, where detection may result in the diagnosis of a condition in the patient from whom the sample was obtained.

Thus, peptide tagged entities may be captured as described above to an immobilised binding partner of the invention and may subsequently be detected using a labelled antibody directed to the entity e.g. by virtue of an ELISA where the detecting antibody may be linked to an enzyme or by immunofluorescence where the antibody may have a fluorescent label, dye or quantum dot. In order to carry out such diagnostic methods, the binding partner of the invention may be immobilised to a plate (e.g. to 12, 24, 48 or 96 well plates).

A particularly preferred use of the peptide tag and binding partner pairs of the present invention is in cell imaging in view of the irreversible binding which occurs. This allows any cells labelled with a peptide tag/binding partner of the invention to be visualised for long periods of time. In this aspect, antibodies which are labelled with a peptide tag of the invention and which are directed to a cell surface protein of interest are bound to cells. The binding partner of the invention which covalently binds to the peptide tag is then subsequently added and will generally be labelled to allow visualisation of the cells e.g. by immunofluorescence where the binding partner may be labelled fluorescently e.g. with a fluorophore. Alternatively, a peptide tag made recombinantly can be added to the binding partner which is expressed on cells Further, the peptide tag and binding partner pairs of the invention may be used in targeting therapeutic agents to tumours. It is possible to label tumour cells using antibodies conjugated to peptide tags of the invention where the antibodies are directed to tumour cell surface antigens. The binding partner of the invention which covalently binds to the peptide tag may be conjugated to a therapeutic agent such as a radioactive isotope and this may then be administered to bind specifically to the peptide tagged tumour cells (rather than to normal cells of the body). The peptide tag and binding partner pairs of the invention are particularly well suited to this application, in view of their irreversible binding to each other. Thus, the binding partner will stay bound to the peptide tag and will ensure that the therapeutic agent is delivered to the tumour cells and that the therapeutic agent is not released from the tumour as a result of peptide dissociation.

The peptide tag and binding partner pairs of the invention can therefore be used to treat cancer or other disease which can be treated by the targeted delivery of a therapeutic agent to particular cells. The invention thus provides a binding partner of the invention conjugated to a therapeutic agent for use in therapy. More particularly, the invention provides a binding partner of the present invention conjugated to a therapeutic agent for treating cancer. As discussed above, the binding partner in these aspects is used to target a therapeutic agent to a cell labelled with a peptide tag of the invention to which the binding partner covalently binds.

Alternatively viewed, the invention provides a method for treating cancer comprising administering a binding partner of the invention conjugated to a therapeutic agent to a subject, wherein said subject has been pre-treated to label cancerous cells with a peptide tag of the invention which is able to covalently bind said binding partner.

The binding partner may also be used in vitro, in order to target an agent to which it is conjugated to cells that have been labelled with a peptide tag of the invention.

BRIEF DESCRIPTION OF THE DRAWINGS

The invention will now be described in more detail in the following non-limiting Examples with reference to the drawings in which:

FIG. 1 shows isopeptide bond formation between Lys and Asn side chains.

FIG. 2 shows key residues for spontaneous isopeptide bond formation in the C-domain of the major pilin from Protein Data Bank file 3B2M.

FIG. 3 shows a cartoon of isopeptag construction. The major pilin was dissected into a large N-terminal fragment and a small C-terminal fragment.

FIG. 4 shows isopeptag and pilin-C associated covalently. Isopeptag-MBP and pilin-C were mixed, incubated for 24 hours at 25° C. at pH 7.0, and analysed by SDS-PAGE with Coomassie staining. Pilin-C K179A is a negative control where the lysine involved in isopeptide bond formation was mutated.

FIG. 5 shows isopeptag-MBP and pilin-C covalent complex with loss of 17 Da indicating isopeptide bond formation.

FIG. 6 shows a time course of isopeptag-MBP and pilin-C reaction at 25° C. pH 7.0 determined by SDS-PAGE.

FIG. 7 shows the temperature dependence of isopeptag-MBP reaction with pilin-C at pH 7.0.

FIG. 8 shows the effect of pH on isopeptag-MBP and pilin-C reaction at 25° C. (all graphs mean of triplicate+/−1 s.d.)

FIG. 9 is a cartoon of the isopeptag-CFP-TM construct targeted by exogenous pilin-C.

FIG. 10 shows HeLa cells expressing isopeptag-CFP-TM were incubated with pilin-C or pilin-C K179A control then reconstitution was detected with anti-His tag antibody and Alexa Fluor 555-secondary antibody.

FIG. 11 shows ilin-C alone. Expression of pilin-C also yields a small amount of covalent pilin-C dimer, visible here by MS (inset) and also visible by SDS-PAGE after boiling (FIG. 4). Pilin-C contains one isopeptide in the N-domain. Based on its mass, the Pilin-C dimer contains two isopeptides, one intramolecular and one intermolecular.

FIG. 12 shows pilin-C K179A alone, the negative control for intermolecular isopeptide bond formation.

FIG. 13 shows isopeptag-MBP alone.

FIG. 14 shows Pilin-C and isopeptag-MBP were mixed at 100 µM for 24 hours at 4° C. in PBS. The covalent complex was observed, corresponding to loss of NH$_3$ (17 Da) upon isopeptide bond formation, as well as some residual isopeptag-MBP.

FIG. 15 shows a negative control, where pilin-C K179A and isopeptag-MBP were mixed as in (FIG. 14) but no high molecular weight complex was detected.

FIG. 16 shows key residues for spontaneous isopeptide formation in the N-domain of the major pilin protein Spy0128 of S. pyogenes, from Protein Data Bank 3B2M.

FIG. 17 shows isopeptag-N construction. Spy0128 was dissected into a small N-terminal fragment and a large C-terminal fragment.

FIG. 18 shows isopeptag-N and pilin-N are able to covalently react in vitro. MBP-isopeptag-N and pilin-N were mixed and incubated for 24 hours at 25° C., pH 7.0. Pilin-N E117A is a negative control, where the Glu essential for promoting covalent reaction was mutated. Reaction was analysed by SDS-PAGE and Coomassie staining. *A side product of pilin-N expression from misformation of the intramolecular isopeptide.

FIG. 19 shows a schematic illustrating the various isopeptag-MBP (SEQ ID NO:s: 33 and 34) and pilin-C constructs (pilin-C-7 and SEQ ID NOs. 35-38) tested. The Spy0128 crystal structure (Protein Data Bank 3B2M) stops at residue F307 and has Val at 306 instead of the Asp in S. pyogenes strain M1 GAS (NCBI Entrez Nucleotide Accession No. AE004092). The isopeptag construct had Asp at residue 306 and the surface exposed Phe at position 307 was changed to Ala to increase solubility. The numbers depict the change in the number of residues compared to the pilin-C and isopeptag-MBP constructs finally chosen and used in all other figures. Including residues from the final β-strand in pilin-C was evaluated on the basis that these residues could inhibit the other two neighbouring β strands interacting with each other and so occluding the isopeptag binding site.

FIG. 20 shows the reconstitution efficiency of the isopeptag-MBP and pilin-C constructs, after incubation at 25° C. for 24 hours in PBS pH 7.4, determined by SDS-PAGE and Coomassie staining. The means of triplicate results are shown+/−1 s.d.

FIG. 23 shows the sequences of SEQ ID NOs 1 to 7.

EXAMPLES

Materials and Methods

Figure 1:
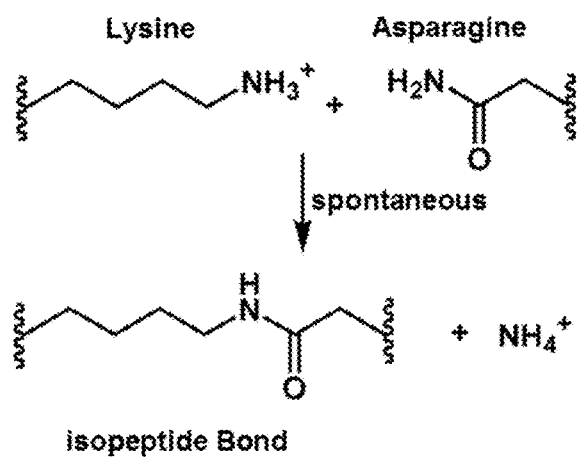
FIGS. 1-4 show spontaneous intermolecular isopeptide bond formation.

Plasmids. All residues numbers are based on the Spy0128 protein. PCR was performed with KOD Hot Start DNA polymerase (Roche) and cycling conditions as recommended by the manufacturer. The Spy0128 gene was PCR-amplified from Streptococcus pyogenes M1 GAS strain SF370 genomic DNA (ATCC 700294D-5) using the primers 5'-GGGGCATATGGCTACAACAGTTCACGGG-3' (SEQ ID NO. 8) and 5'-GGGGAAGCTTTTAT-TCAAAGTCTTTTTTATTTG-3' (SEQ ID NO. 9), and subsequently cloned in to pET28a (Novagen) using the restriction enzymes NdeI and HindIII. To construct isopeptag-MBP, isopeptag (Spy0128 residues 293-308) was PCR-amplified from pET28a-Spy0128 using the primers 5'-GGGGCATATGGGAACTGATAAAGATATGACC-3' (SEQ ID NO. 10) and 5'-ACCACTTTCACCACTACCT-TCAAAGTCTTTTTTATTTG-3' (SEQ ID NO. 11) while the Maltose Binding Protein (MBP) was amplified from pMAL (New England Biolabs) using the primers 5'-AAGG-TAGTGGTGAAAGTGGTAAAATCGAAGAAGGTAAA-3' (SEQ ID NO. 12) and 5'-GGGGAAGCTTTTAC-GAGCTCGAATTAGTCTG-3'. (SEQ ID NO. 13) The two fragments were joined by overlap extension PCR, and cloned in to pET28a using NdeI and HindIII sites. This gave a GSGESG linker. The final isopeptag-MBP construct was generated by a further mutation of F307A (based on the complete Spy0128 sequence), to remove an exposed hydrophobic residue, using the QuikChange™ (Stratagene) protocol with KOD Hot Start DNA polymerase and the primer 5'-TTTACAAATAAAAAAGACGCTGAAGGTAGTGGT-GAAAG-3' (SEQ ID NO. 14) and its reverse complement.

To generate isopeptag-MBP-5 (Spy0128 residues 298-308), the sequence was PCR amplified from pET28a-isopeptag-MBP using primers 5'-GGGCATATGGGAACCAT-TACTTTTACAAAT-3' (SEQ ID NO. 15) and 5'-GGGGAAGCTTTTACGAGCTCGAATTAGTCTG-3' (SEQ ID NO. 16) and cloned in to pET28a using NdeI and HindIII sites.

To generate pilin-C(Spy0128 residues 18-299), a stop codon was introduced at residue 300 in the pET28a-Spy0128 using the primer 5'-ACAAGAGACATCTACT-GATAAAGATATGACCATTTAGTTTA-CAAATAAAAAAGACTTTGAATAAAAGCTTG-3' (SEQ ID NO. 17) and its reverse complement.

To generate pilin-C K179A from pET28a-Spy0128, we used the primer 5'-TCTACTACATTAACGGT-GAAGGCAAAAGTTTCAGGTACCGGTGG-3' (SEQ ID NO. 18) and its reverse complement, and then a stop codon was introduced at residue 300 in pET28a-Spy0128 using the primer 5'-ACAAGAGACATCTACTGATAAAGATAT-GACCATTTAGTTTACAAATAAAAAAGACTTT-GAATAAAAGCTTG-3' (SEQ ID No. 19) and its reverse complement.

To generate pilin-C-7 (Spy0128 residues 18-292), a stop codon was introduced at residue 293 in pET28a-Spy0128 using the primer 5'-GCAGGTAATTCAACTGAACAAGA-GACATCTTAGGATAAAGATATGACCATTACTTTTA-CAAAT-3' (SEQ ID NO. 20) and its reverse complement.

To generate pilin-C-2 (Spy0128 residues 18-297), a stop codon was introduced at residue 298 in pET28a-Spy0128 using the primer 5'-ACTGAACAAGAGACATCTACTGA-TAAAGATATGTAGATTACTTTTA-CAAATAAAAAAGACTTTGAAGTG-3' (SEQ ID NO. 21) and its reverse complement.

To generate pilin-C-1 (Spy0128 residues 18-298), a stop codon was introduced at residue 299 in pET28a-Spy0128 using the primer 5'-GAACAAGAGACATCTACTGA-TAAAGATATGACCTAGACTTTTA-CAAATAAAAAAGACTTTGAATAAAAG-3' (SEQ ID NO. 22) and its reverse complement.

To generate pilin-C+1 (Spy0128 residues 18-300), a stop codon was introduced at residue 301 in pET28a-SPy0128 using the primer 5'-CAAGAGACATCTACTGATAAAGA-TATGACCATTACTTAGACAAATAAAAAAGACTTT-GAATAAAA-3' (SEQ ID NO. 23) and its reverse complement.

To construct MBP-isopeptag-N, isopeptag-N(Spy0128 residues 18-45) was PCR amplified from pET28a-Spy0128 using the primers 5'-CTAATTCGAGCTCGGGTTCGGGT-GAAAGTGGTGCTACAACAGTTCACGGG-3'-(SEQ ID NO. 24) and 5'-GGGGAAGCTTTTATGCATTGCTAT-TAACTAAATC-3'-(SEQ ID NO. 25), while MBP was amplified from pMAL using primers 5'-CAAGCATAT-GAAAATCGAAGAAG-3' (SEQ ID NO. 26) and 5'-CGAACCCGAGCTCGAATTAGTCTG-3' (SEQ ID NO. 27). The two fragments were joined using overlap extension PCR, and cloned in to pET28a at NdeI and HindIII sites. Pilin-N(Spy0128 residues 46-308) was generated from pET28a-Spy0128 using the primers 5'-GGGGCATATGGGATTAATTCCAAATACAGAT—3' (SEQ ID NO. 28) and 5'-GGGGAAGCTTCTAGTGATG-GTGATGGTGATGTCCTGATCCTTCAAAGTCTTTTTT-ATTTG-3' (SEQ ID NO: 29)_, and subsequently cloned in to pET28a using NdeI and HindIII sites. Pilin-N E117A was generated from pET28a-pilin-N using the primer 5'-GTGTT-TATTATTACAAAGTAACTGCGGAGAAGATAGA-TAAAGTTCCTGG-3' (SEQ ID NO. 30) and its reverse complement.

Isopeptag-CFP-TM was based on pDisplay (Invitrogen). 5'-GACAGATCTGGCGGCACTGATAAAGATATGAC-CATTACTTTTACAAATAAAAAAGACTTTGAAGG-TAGTGGTATGGTGAGCAAGGGCGAG-3' (SEQ ID NO. 31) and 5'-ACTCTCGGCATGGACGAGCTATA-CAAGCGGCCGCGGGGAG-3' (SEQ ID NO. 32) were used for PCR from AP-CFP-TM (Chen et al., 2005). The PCR product was gel purified and inserted in the BglII and SacII sites of pDisplay. We verified all constructs and mutations by sequencing. The nuclear co-transfection marker pECFP-H2B (human histone H2B for nuclear localisation fused to enhanced cyan fluorescent protein) was constructed as described in Platani et al, Nat. Cell Biol., 2002, 4, 502-508.

Protein Expression

All proteins were expressed using E. coli BL21 DE3 RIPL cells (Stratagene), grown in LB with 0.8% glucose and 0.05 mg/mL kanamycin. We diluted overnight cultures 100-fold, grew at 37° C. to $A_{600}$ 0.5, and induced with 0.4 mM IPTG for 4 hr at 30° C. All proteins were purified by nickel affinity chromatography, using standard methods, and dialysed into PBS. Protein concentration was determined from $A_{280}$, using the extinction coefficient predicted by ExPASy ProtParam. Typical expression yields per L of culture were 12 mg for pilin-C and 20 mg for isopeptag-MBP.

SDS-Page

SDS-PAGE was performed on 12% polyacrylamide gels, using an X-cel SureLock (Invitrogen) at 200 V. Samples were heated at 95° C. for 7 min in SDS loading buffer on a Bio-Rad C1000 thermal cycler before loading. Gels were stained with Coomassie brilliant blue, destained in 60% MilliQ water, 30% methanol and 10% acetic acid, and band intensities were quantified using a ChemiDoc XRS imager and QuantityOne 4.6 software (Bio-Rad).

Reconstitution Reactions

Reactions for analysis of speed, temperature dependence and pH dependence of isopeptide bond formation by SDS-PAGE were performed with 10 μM of each protein in 40 mM $Na_2HPO_4$-20 mM citric acid at the indicated pH. For analysing isopeptide bond formation in various buffers and detergent, 10 μM of pilin-C and 10 μM of isopeptag-MBP were mixed in either PBS pH 7.4, 40 mM $Na_2HPO_4$-20 mM citric acid pH 7.4, 50 mM Tris (tris(hydroxymethyl)aminomethane) pH 7.4, or 50 mM HEPES (4-(2-hydroxyethyl)-1-peperazine ethanesulfonate) pH 7.4, and also in the presence and absence of 1% Triton X-100 or 0.5% Nonidet P-40.

pH for all buffers was adjusted with 1M NaOH or 1M HCl, except for HEPES which was adjusted with 1M KOH (to establish whether $Na^+$ was required for reaction). Reactions were stopped by adding SDS loading buffer and heating at 95° C. for 7 min. For 4° C. reactions, samples were incubated in the refrigerator, and for 25° C. and 37° C. samples were incubated on a Bio-Rad C1000 thermal cycler with a heated lid to prevent evaporation. The yield of isopeptide bond formation was calculated from the average of triplicate reaction by determining band intensity. The percent covalent complex formation between pilin-C and isopeptag-MBP at about 80 kDa was calculated by dividing the density of the band for the covalent complex by the sum of the density of all the bands in the lane, then multiplying by 100.

Mass Spectrometry

Mass spectrometry was performed with a Micromass LCT time-of-flight spectrometer (Micromass UK). 100 μM of each protein was mixed in PBS pH 7.4 and incubated at 4° C. for 24 hours. The reactions were then dialysed against MilliQ $H_2O$ using 0.025 μM VSWP Millipore membrane filters (VSWP 01300) for 1 hr at 25° C.

The reactions were then further de-salted using Millipore ZipTip pipette tips (ZTC04S096). The m/z spectrum was converted to a molecular mass profile using Maximum Entropy processing by the software MassLynx V4.00.00. Predicted masses were determined by ExPASy ProtParam.

Cell Culture, Labeling and Microscopy

HeLa cells were grown in DMEM with 10% Foetal Calf Serum, 50 U/mL penicillin, and 50 μg/mL streptomycin. Cells were transfected using 0.75 μL Lipofectamine 2000 (Invitrogen) and 0.3 μg of isopeptag-CFP-TM per well of a 48-well plate, according to manufacturer's instructions. 1 day after transfection, cells were incubated with 5 μM of either pilin-C or pilin-C K179A and incubated at 37° C. for 4 hr. Cells were then stained at 4° C. as follows: wash 3× with PBS+5 mM $MgCl_2$ (PBS-Mg), add 100 μL of 11 μg/mL penta-His antibody (Qiagen) in PBS-Mg and 1% BSA and incubate for 10 min, wash 3× with PBS-Mg, add 100 μL of 20 μg/mL Alexa Fluor 555-anti-mouse antibody (Invitrogen) in PBS-Mg and 1% BSA and incubate for 10 min, wash 3× with PBS-Mg, add 100 μL fixing solution (PBS containing 4% formaldehyde, 4% sucrose and 5 mM $MgCl_2$) for 10 min and then wash 3 times with PBS-Mg. Cells were imaged using a wide-field DeltaVision Core fluorescent microscope (AppliedPrecision) with a 40× oil-immersion lens. ECFP (436DF20 excitation, 480DF40 emission, Chroma 86002v1 dichroic) and Alexa Fluor 555 (540D420 excitation, 600DF50 emission, Chroma 84100bs polychroic) images were collected and analysed using softWoRx 3.6.2 software.

Typical exposure times were 0.1-1.0 s and fluorescence images were background-corrected. Different samples in the same experiment were prepared, imaged and analysed under identical conditions.

Results

Design of the Isopeptag and Reconstitution In Vitro

To generate a peptide fragment with significant affinity for its partner protein, while minimising disruption to the parent protein, S. pyogenes major pilin (Spy0128) was split at residue 299 in the final β-strand of the C-terminal domain, to give the fragment pilin-C (Spy0128 residues 18-299, with an N-terminal His6 tag) and the isopeptag (Spy0128 residues 293-308). This placed the reactive asparagine on the isopeptag and the reactive lysine on pilin-C. To enhance recombinant protein expression in E. coli, the isopeptag was genetically fused to the N-terminus of Maltose Binding Protein (MBP).

Figure 2:
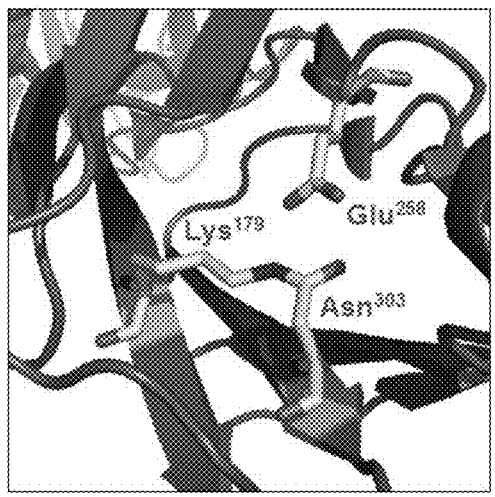

To test covalent reaction, isopeptag-MBP and pilin-C were mixed and the samples boiled before SDS-PAGE (FIG. 1D). A new product formed at ~80 kDa, consistent with reaction between isopeptag-MBP and pilin-C, with a yield of 50-60%. Isopeptide bond formation was verified between isopeptag-MBP and pilin-C by mass spectrometry, demonstrating the loss of $NH_3$ upon reaction (FIG. 2A).

Figure 4:
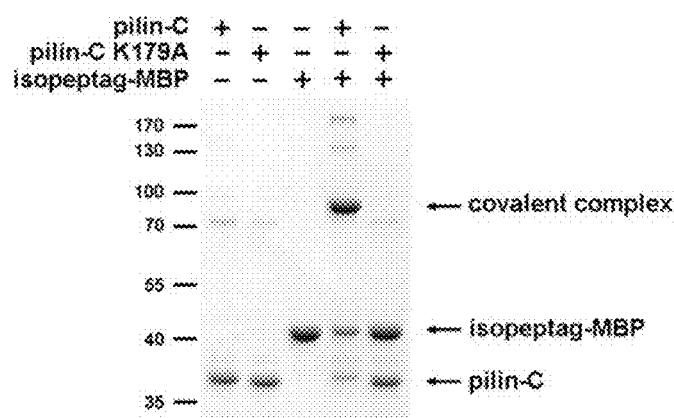

As a control, a pilin-C K179A mutant was constructed, removing the reactive lysine. As expected, this mutant was unable to form a covalent complex with isopeptag-MBP by SDS-PAGE (FIG. 1D) and mass spectrometry (FIG. 4).

Figure 5:
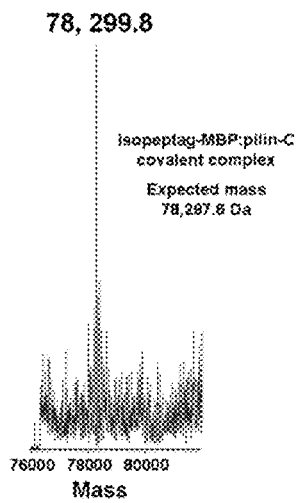
FIGS. 5-8 show the characterisation of spontaneous isopeptide bond formation.

Spy0128 contains an alternative isopeptide in its N-terminal domain (FIG. 5A). The generality of the strategy for splitting spontaneous isopeptide bond forming peptides was shown by dissecting Spy0128 at its N-terminal β strand, placing the reactive lysine on the peptide fragment (isopeptag-N) and the reactive asparagine on the protein fragment (pilin-N) (FIG. 5B). Isopeptag-N and pilin-N also covalently reconstituted when mixed (FIG. 5C).

Characterisation of Isopeptag Reactivity

Figure 6:
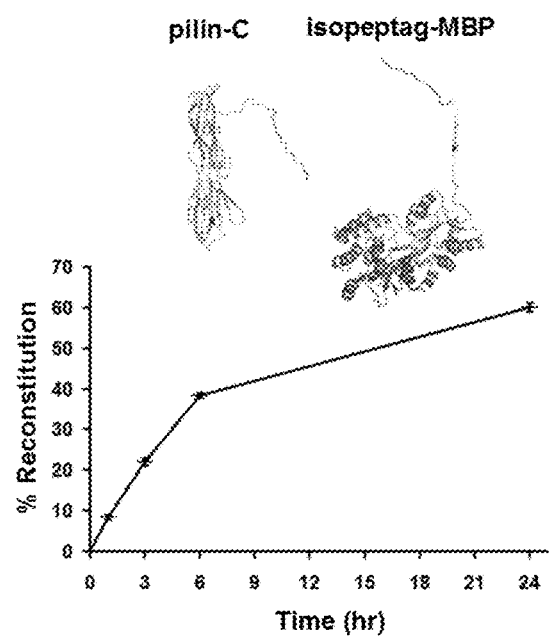

To determine the exact features of pilin-C and isopeptag that are important for reaction, pilin-C was truncated earlier or later in the final β strand: this did not substantially change reactivity (FIG. 6). On the other hand, truncating the isopeptag by the 5 residues that comprised the loop preceding the final β strand dramatically reduced reaction (FIG. 6).

Figure 7:
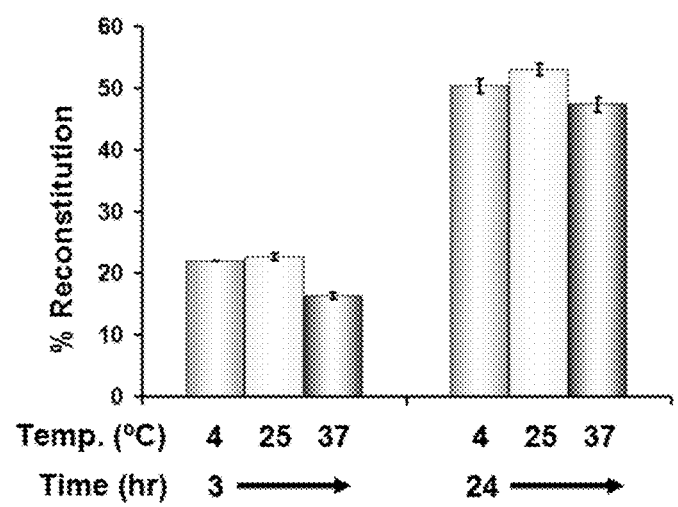
Figure 8:
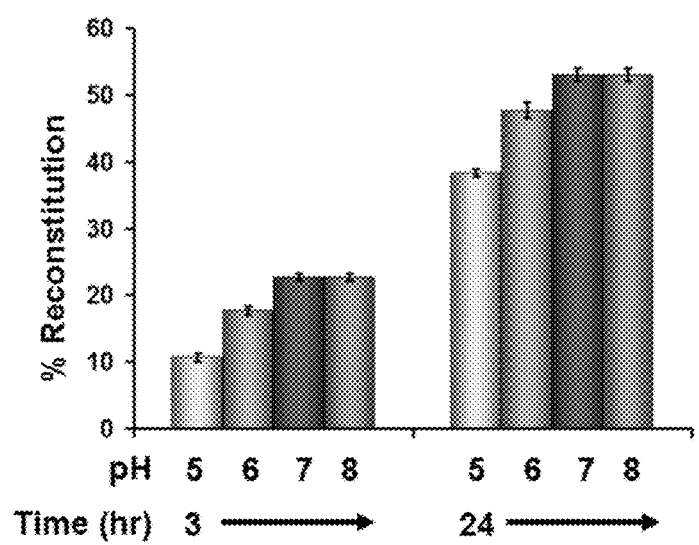
Figure 9:
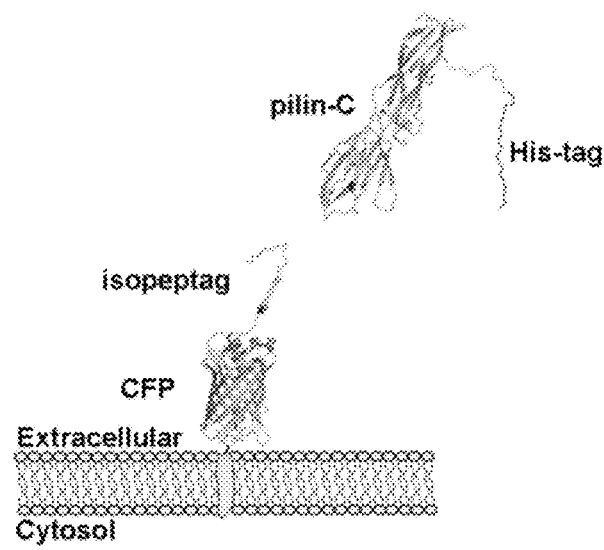
FIGS. 9 and 10 show the specificity of isopeptag on mammalian cells.
Figure 10:
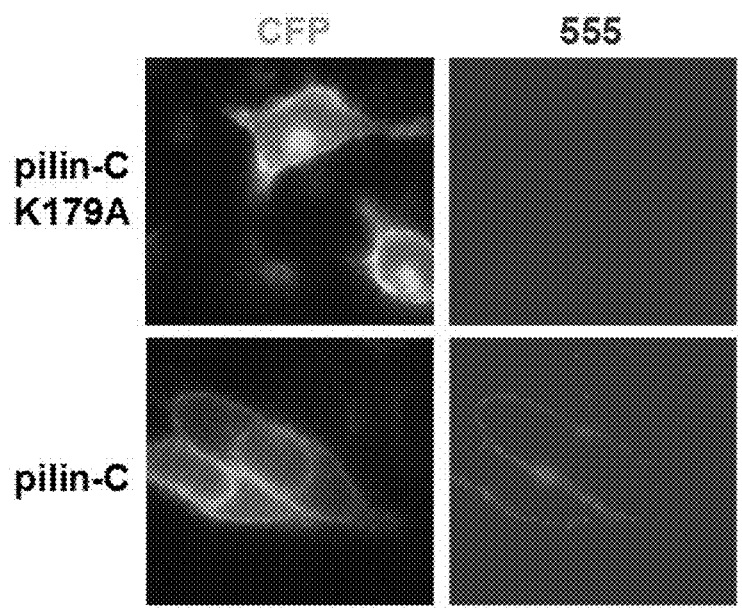
Figure 11:
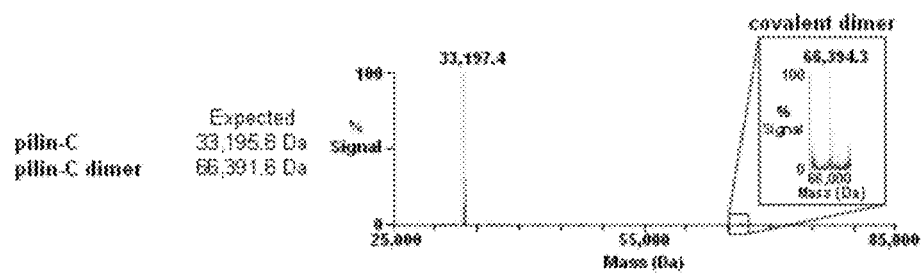
FIGS. 11-15 show mass spectrometry of spontaneous intermolecular isopeptide bond formation.
Figure 12:
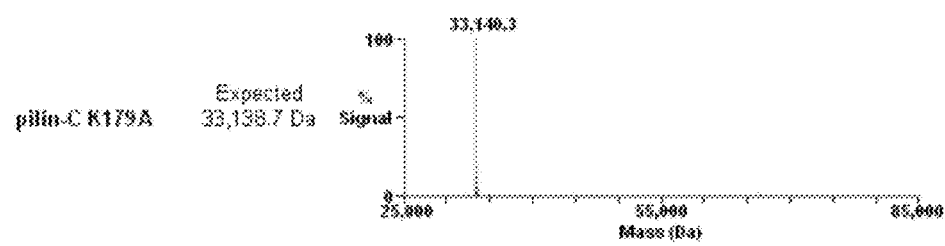
Figure 13:
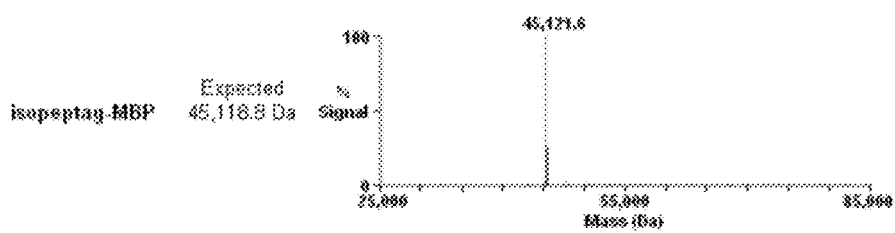
Figure 14:
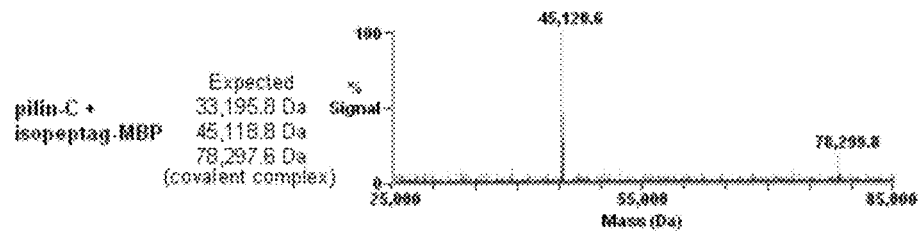
Figure 15:
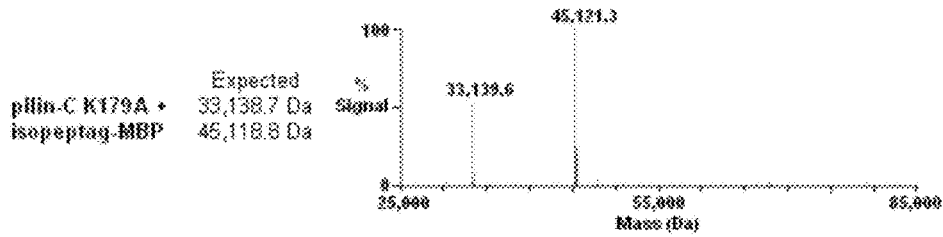
Figure 16:
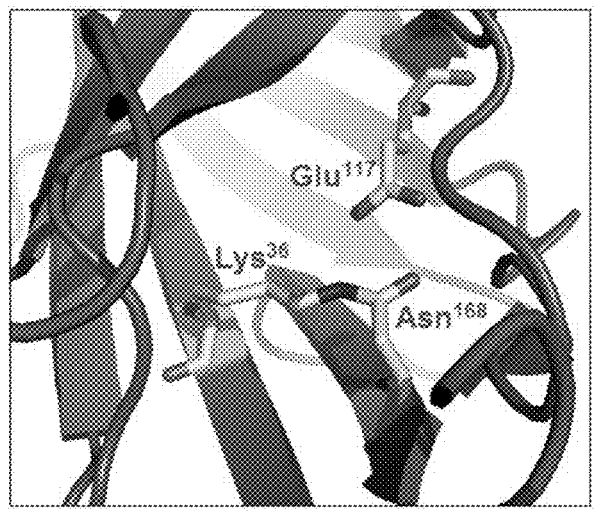
FIGS. 16-18 show an alternative spontaneous intermolecular isopeptide bond-forming peptide.
Figure 17:
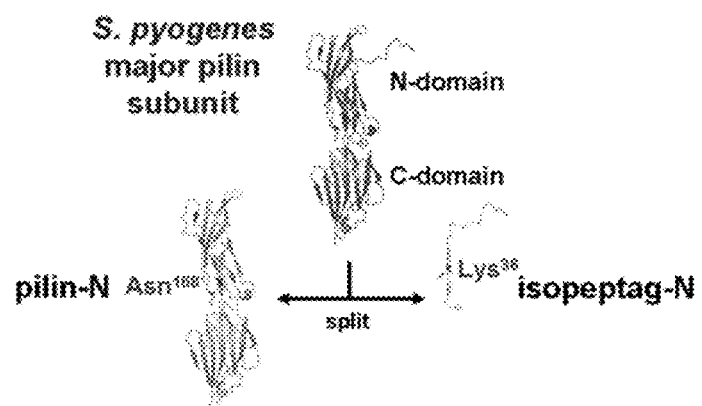
Figure 18:
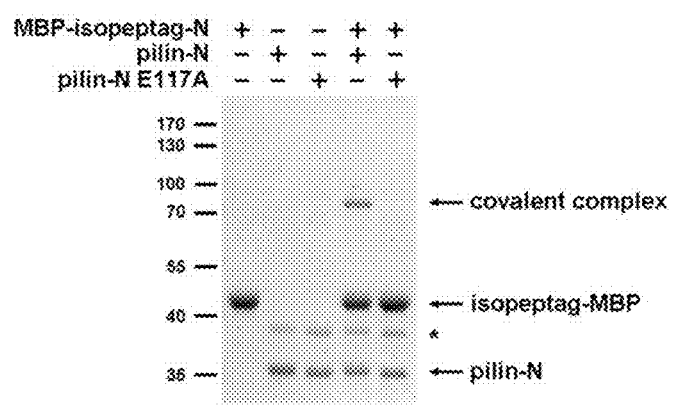
Figure 19:
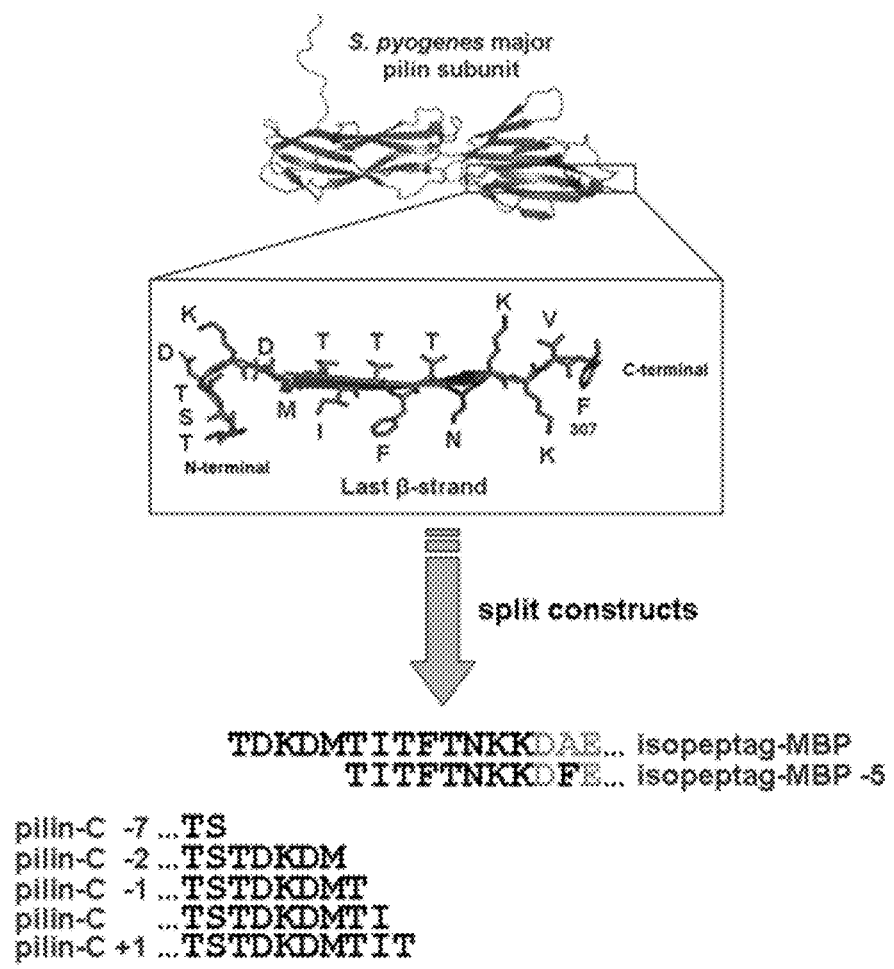
FIGS. 19 and 20 show optimisation of split pilin constructs to generate isopeptag and pilin-C.
Figure 20:
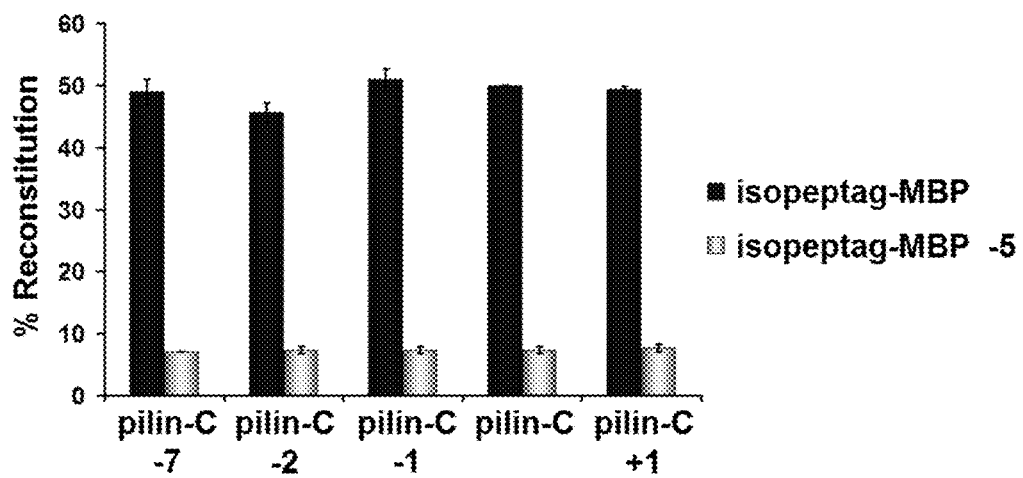
Figure 21:
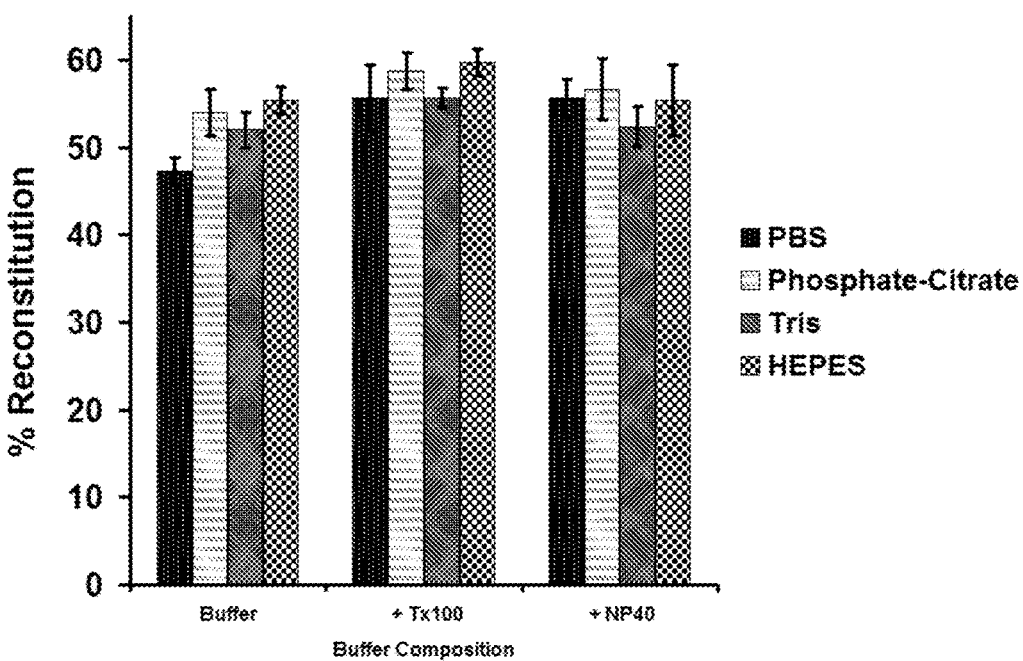
FIG. 21 shows that spontaneous isopeptide bond formation occurred in diverse buffers. Isopeptag-MBP and pilin-C each at 10 µM were mixed in the indicated buffer with or without the common biological detergents Triton X-100 (Tx100) or Nonidet P-40 (NP40) and incubated for 24 hours at 25° C. pH 7.0. Detergent might have been expected to change the rate of reaction, if isopeptide bond formation depended on exposure of a hydrophobic part of pilin-C. PBS is phosphate buffered saline. Reaction was determined by SDS-PAGE with Coomassie staining. The means of triplicate results are shown+/−1 s.d.
Figure 22:
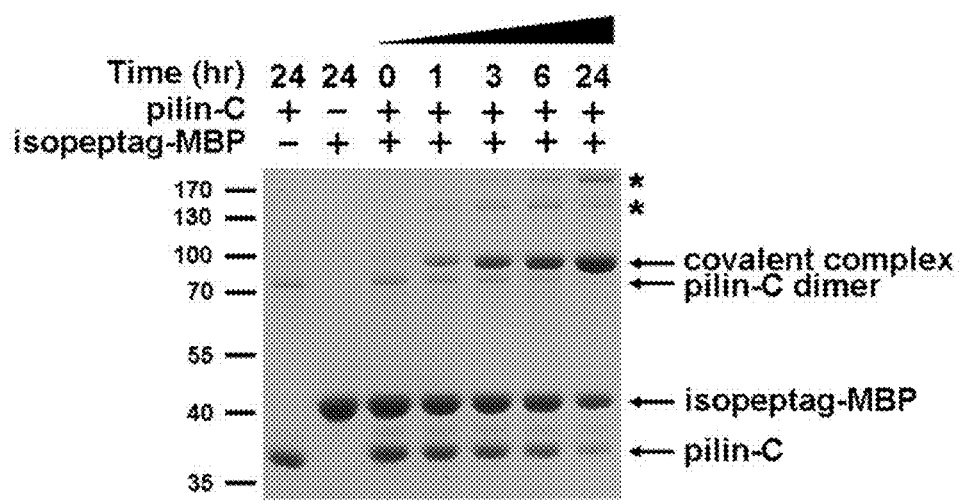
FIG. 22 shows the time-course of spontaneous bond formation by SDS-PAGE. Isopeptag-MBP and pilin-C were mixed at 10 µM and incubated at 25° C., pH 7.0. The reaction was stopped at varying times and analysed by SDS-PAGE with Coomassie staining. *The side product likely relates to the pilin-C dimer reacting with 1 or 2 isopeptag-MBP.

The speed of isopeptide bond formation was tested. Reaction was detectable after 10 min, nearly complete at 6 hours, and reached a plateau at 24 hours (FIG. 2B). The range of conditions for isopeptag-MBP and pilin-C covalent reaction was explored. Surprisingly, the yield and speed of reaction was largely temperature-independent from 4-37° C. (FIG. 2C). Reaction was also largely independent of pH from 6-8 but was reduced by 15% at pH 5 after 24 hours (FIG. 2D). The isopeptag reaction proceeded to a similar extent in all buffers tested, with no requirement for any particular monovalent or divalent ions (FIG. 7). Conditions that prevent spontaneous bond formation have not been found.

The rate of intramolecular Lys-Asn bond formation has not been determined because the reaction had gone to completion when the pilin was isolated but it is likely to be substantially faster than the typical 25 min generation time of S. pyogenes; future screening of phage display libraries may be able to identify isopeptag variants that associate rapidly and approach the intramolecular rate of reaction.

Figure 3:
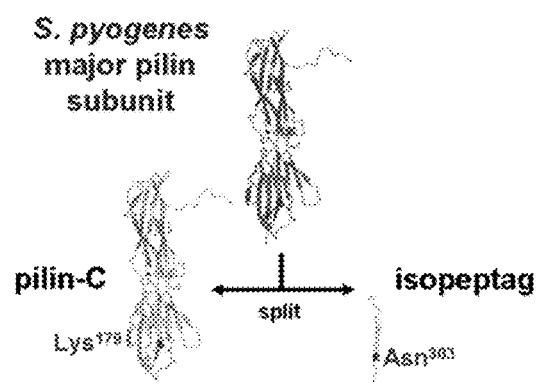

To test the specificity of spontaneous isopeptide bond formation in a complex environment, the isopeptag was targeted to the surface of mammalian cells (FIG. 3A). Isopeptag-CFP-TM was labelled by pilin-C but no binding was detected by the control pilin-C K179A (FIG. 3B), indicating good specificity of isopeptide formation.

The invention claimed is:

1. A binding partner comprising a fragment of an isopeptide protein selected from the group consisting of:
 (i) FbaB protein from *Streptococcus pyogenes* as set forth in SEQ ID NO: 6, or a protein with at least 80% identity thereto capable of spontaneously forming an isopeptide bond; and
 (ii) major pilin protein Spy0128 from *Streptococcus pyogenes* as set forth in SEQ ID NO:1, or a protein with at least 95% identity thereto capable of spontaneously forming an isopeptide bond,
 wherein said fragment is at least 20 amino acids in length and has only one reactive residue involved in the formation of an intramolecular isopeptide bond in said isopeptide protein and is capable of binding to a peptide tag by forming an isopeptide bond between said reactive residue and a reactive residue in said peptide tag, wherein said peptide tag has a length of at least 5 amino acids but no more than 50 amino acids and comprises:
 (a) a fragment of the isopeptide protein of (i) wherein an aspartic acid is present at a position that corresponds to position 101 of SEQ ID NO: 6; or
 (b) a fragment of the isopeptide protein of (ii) comprising residues 302-308 of the sequence set out in SEQ ID NO: 1,
 wherein said binding partner is conjugated to a nucleic acid molecule, protein, peptide, small-molecule organic compound, fluorophore, metal-ligand complex, polysaccharide, nanoparticle, nanotube, polymer or a combination thereof.

2. The binding partner of claim 1, wherein said binding partner comprises a fragment of an isopeptide protein of a sequence with at least 80% identity to SEQ ID NO: 6, wherein a lysine is present at a position corresponding to position 15 of SEQ ID NO: 6, and wherein said binding partner is capable of binding to a peptide tag by forming an isopeptide bond between said lysine residue and an aspartic acid residue in said peptide tag, wherein said peptide tag has a length of at least 5 amino acids but no more than 50 amino acids and comprises a fragment of the isopeptide protein of (i) wherein an aspartic acid is present at a position that corresponds to position 101 of SEQ ID NO: 6.

3. The binding partner of claim 1, wherein said binding partner comprises a fragment of SEQ ID NO: 6 comprising the lysine at position 15 of SEQ ID NO: 6, and wherein said binding partner is capable of binding to a peptide tag by forming an isopeptide bond between said lysine residue and an aspartic acid residue in said peptide tag, wherein said peptide tag has a length of at least 5 amino acids but no more than 50 amino acids and comprises a fragment of the isopeptide protein of (i) wherein an aspartic acid is present at a position that corresponds to position 101 of SEQ ID NO: 6.

4. The binding partner of claim 1, wherein said binding partner is a fragment of an isopeptide protein comprising a sequence with at least 95% identity to residues 31-291 of the sequence set out in SEQ ID NO: 1, wherein said binding partner is capable of binding to a peptide tag by forming an isopeptide bond between said reactive residue and a reactive residue in said peptide tag, wherein said peptide tag has a length of at least 5 amino acids but no more than 50 amino acids and comprises a fragment of the isopeptide protein of (ii) comprising residues 302-308 of the sequence set out in SEQ ID NO: 1.

* * * * *